(12) United States Patent
Saito et al.

(10) Patent No.: US 6,340,751 B1
(45) Date of Patent: Jan. 22, 2002

(54) PROCESS FOR THE PREPARATION OF 4-SUBSTITUTED AZETIDINONE DERIVATIVES

(75) Inventors: Takao Saito; Toshiyuki Murayama; Takaji Matsumoto; Takashi Miura, all of Kanagawa (JP)

(73) Assignee: Takasago International Corporation, Tokyo (JP)

( * ) Notice: Subject to any disclaimer, the term of this patent is extended or adjusted under 35 U.S.C. 154(b) by 0 days.

(21) Appl. No.: 09/357,153

(22) Filed: Jul. 19, 1999

(30) Foreign Application Priority Data

Jul. 24, 1998 (JP) .......................... 10-223724

(51) Int. Cl.$^7$ .................. C07F 7/18; C07D 205/08; C07D 227/087; C07D 413/06
(52) U.S. Cl. .................. 540/200; 548/216; 548/221; 548/225; 548/230; 548/551; 544/71; 544/97
(58) Field of Search ........................ 540/200

(56) References Cited

U.S. PATENT DOCUMENTS

| | | | |
|---|---|---|---|
| 5,442,055 A | 8/1995 | Iwasaki et al. | 540/200 |
| 5,550,229 A | 8/1996 | Iwasaki et al. | 540/200 |
| 5,631,363 A | 5/1997 | Iwasaki et al. | 540/71 |
| 5,703,234 A | 12/1997 | Iwasaki et al. | 544/50 |
| 5,731,431 A | 3/1998 | Nakagawa et al. | 540/200 |
| 5,792,861 A | 8/1998 | Hara et al. | 540/200 |
| 5,847,115 A | 12/1998 | Iwasaki et al. | 540/200 |

OTHER PUBLICATIONS

Fuentes, JACS 108, 4675, 1986.*
Dictionary of Science and Technology, Academic Press (1995)—online version.
Webster's Third New International Dictionary, Merriam–Webster (1993) p. 2120.
Berks "Preparation of Two Pivoted Intermediates for the Synthesis of 1–β–Methyl Carbapenem Antibiotics"—*Tetrahedron*, vol. 52, No. 2, pp. 331–375, 1996.

* cited by examiner

Primary Examiner—Mark L. Berch
(74) Attorney, Agent, or Firm—Sughrue Mion, PLLC

(57) ABSTRACT

Disclosed is a process for the preparation of a 4-substituted azetidinone derivative, which comprises reacting an azetidinone derivative and an amide compound in the presence of a magnesium compound such as those represented by the following formulas (II):

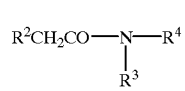

(II)

and (IV):

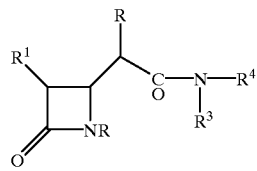

(IV)

represented by the following formula (III):

$$MgR^5R^6 \quad \text{(III)}$$

wherein $R^5$ represents a $C_{1-12}$ alkyl group, a $C_{2-5}$ alkenyl group, a 5- to 8-membered alicyclic group which may be substituted by a lower $C_{1-4}$ alkyl group, a phenyl group which may be substituted by a lower $C_{1-4}$ alkyl group, a lower $C_{1-4}$ alkoxy group or a halogen atom or a benzyl group which may be substituted by a lower $C_{1-4}$ alkyl group, a lower $C_{1-4}$ alkoxy group or a halogen atom, and $R^6$ represents a halogen atom, a methanesulfonyloxy group, a benzenesulfonyloxy group, a p-toluenesulfonyloxy group, a trifluoromethanesulfonyloxy group, an acetoxy group which may be substituted by a halogen atom or a cyano group or an $OR^7$ group ($R^7$ representing a lower $C_{1-4}$ alkyl group, a substituted or unsubstituted phenyl group or a substituted or unsubstituted benzyl group). The process provides an industrially excellent process for the preparation of a 4-substituted azetidinone derivative which permits the selective preparation of an intermediate for the synthesis of a carbapenem antibacterial agent having a desired 1-β' configuration.

27 Claims, No Drawings

PROCESS FOR THE PREPARATION OF 4-SUBSTITUTED AZETIDINONE DERIVATIVES

FIELD OF THE INVENTION

The present application is based on Japanese Application No. Hei. 10-223724, which is incorporated herein by reference.

The present invention relates to a process for the preparation of a 4-substituted azetidinone derivative which is important as an intermediate for the synthesis of a carbapenem compound.

BACKGROUND OF THE INVENTION

Since a 1-β-methylcarbapenem derivative exhibits excellent antibacterial activity against a wide range of bacteria including Gram positive bacteria and Gram negative bacteria and has excellent in vivo stability, it has attracted attentions as an antibacterial agent. For the synthesis of this 1-β-methylcarbapenem derivative, various processes are known. In particular, an azetidinone compound having a β-methyl group at the 1'-position of the 4-side chain, said compound being represented by the following formula (A):

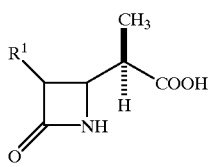

(A)

wherein $R^1$ represents a lower alkyl group which may be substituted by a protected or unprotected hydroxyl group, is an especially important intermediate for the synthesis of the derivative. It has so far been synthesized by a 1'-deprotonation of the acetic acid residue at the 4-position by using a strong base and then introducing a methyl group [*Heterocycles*, 21, 29(1984)]. By the above-described process, however, it is difficult to stereo-selectively prepare a compound having a β-configuration at the 1'-position of the 4-side chain. Various processes are therefore proposed now.

For example, Fuentes, et al. has proposed a process in which a 4-acetoxyazetidinone compound and a certain propionamide derivative are reacted in the presence of a reagent complex composed of a certain base and a Lewis acid, for example, tin triflate—ethylpiperidine—zinc bromide or diethylborane triflate—diisopropylethylamine—zinc bromide [L. M. Fuentes, et al., *J. Am. Chem. Soc.*, 108, 4675(1986), JP-A-61-275267 (the term "JP-A" as used herein means an "unexamined published Japanese patent application")]. A similar process has been proposed by Nagao, et al. [Y. Nagao, et al., *J. Am. Chem. Soc.*, 108, 4673(1986), JP-A-63-170377] and also by Hara, et al. [WO 93/13064, JP-A-7-70116]. Iwasaki, et al. has proposed a process in which reaction is performed in the presence of a predetermined base [JP-A-7-97381].

The above-described process using a reagent complex of a base and a Lewis acid however lacks in environmental harmony because as the Lewis acid, that containing an expensive boron reagent or a heavy metal is employed. It is therefore impossible to deny the industrial disadvantage of this process. In addition, the use of a predetermined base, for example, a base typically employed in this is reaction such as sodium or lithium brings about a marked decrease in the yield under the reaction conditions at around room temperature. Very low temperature conditions at −60° C. or lower become essential, which also makes the process industrially disadvantageous.

With a view to overcoming the above-described problems of the conventional process and to finding a process permitting the selective preparation of an intermediate for the synthesis of a carbapenem antibacterial agent having a desired 1'-β configuration, the present inventors have proceeded with various investigations. As a result, it has been found that a compound having a desired 1'-β configuration can be prepared only by reacting in the presence of a predetermined magnesium compound without using a reagent complex of a base and a Lewis acid as described in the conventional process or without using a base requiring predetermined low-temperature reaction conditions.

SUMMARY OF THE INVENTION

In the present invention, there is provided a process for selectively preparing a desired 1'-β configuration, which comprises reacting an azetidinone compound and a predetermined alkanamide compound in the presence of a magnesium compound without using a reagent complex composed of a base and a Lewis acid or a base which requires predetermined low-temperature reaction conditions.

Described specifically, the present invention provides a process for the preparation of a 4-substituted azetidinone derivative represented by the following formula (IV):

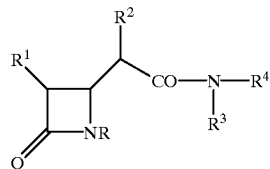

(IV)

wherein R represents a hydrogen atom or a protecting group for N, $R^1$ represents a lower alkyl group which may be substituted by a protected or unprotected hydroxyl group, $R^2$ represents a hydrogen atom or a lower $C_{1-4}$ alkyl group, $R^3$ represents (1) a $C_{1-12}$ alkyl group, (2) a $C_{2-5}$ alkenyl group, (3) a $C_{1-6}$ organosilyl group, (4) a phenyl group which may be substituted by a lower $C_{1-4}$ alkyl group, a lower $C_{1-4}$ alkoxy group, a nitro group or a halogen atom, (5) a $C_{6-13}$ aralkyl group which may be substituted by a lower $C_{1-4}$ alkyl group, (6) a 5- to 8-membered alicyclic group which may be substituted by a lower $C_{1-4}$ alkyl group or (7) a naphthyl group, and $R^4$ represents an electron withdrawing group; or $R^3$ and $R^4$ may form a heterocyclic ring together with the adjacent nitrogen atom, which comprises reacting an azetidinone derivative represented by the following formula (I):

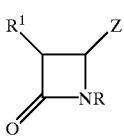

(I)

wherein R represents a hydrogen atom or a protecting group for N, $R^1$ has the same meaning as described above, Z represents an eliminative group, with an amide compound represented by the following formula (II):

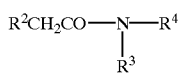
(II)

wherein $R^2$, $R^3$ and $R^4$ have the same meanings as described above,
in the presence of a magnesium compound represented by the following formula (III):

(III)

wherein $R^5$ represents (1) a $C_{1-12}$ alkyl group, (2) a $C_{2-5}$ alkenyl group, (3) a 5- to 8-membered alicyclic group which may be substituted by a lower $C_{1-4}$ alkyl group, (4) a phenyl group which may be substituted by a lower $C_{1-4}$ alkyl group, a lower $C_{1-4}$ alkoxy group or a halogen atom, or (5) a benzyl group which may be substituted by a lower $C_{1-4}$ alkyl group, a lower $C_{1-4}$ alkoxy group or a halogen atom, and $R^6$ represents (1) a halogen atom, (2) a methanesulfonyloxy group, (3) a benzenesulfonyloxy group, (4) a p-toluenesulfonyloxy group, (5) a trifluoromethanesulfonyloxy group, (6) an acetoxy group which may be substituted by a halogen atom or a cyano group, or (7) an $OR^7$ group wherein $R^7$ represents a lower $C_{1-4}$ alkyl group, a substituted or unsubstituted phenyl group or a substituted or unsubstituted benzyl group.

DETAILED DESCRIPTION OF THE INVENTION

The present invention will next be described more specifically.

In the formula (I) of the present invention, R represents a hydrogen atom or a protecting group for N, $R^1$ represents a lower alkyl group which may be substituted by a protected or unprotected hydroxyl group and Z represents an eliminative group.

Specific examples of the protecting group for N include organosilyl groups such as tert-butyldimethylsilyl, tert-butyldiphenylsilyl, triethylsilyl, dimethylcumylsilyl, triisopropylsilyl, dimethylhexylsilyl and dimethylthexylsilyl, a benzyl group, a p-nitrobenzyl group, a p-nitrobenzoylmethyl group, a benzhydryl group, a p-methoxybenzyl group and a 2,4-dimethoxybenzyl group.

Specific examples of the protecting group for the hydroxyl group which is a substituent of the lower alkyl group represented by $R^1$ include organosilyl groups such as tert-butyldimethylsilyl, tert-butyldiphenylsilyl, triethylsilyl, dimethylcumylsilyl, triisopropylsilyl, dimethylhexylsilyl, trimethylsilyl and dimethylthexylsilyl; oxycarbonyl groups such as p-nitrobenzyloxycarbonyl, p-methoxybenzyloxycarbonyl and allyloxycarbonyl; an acetyl group; a triphenylmethyl group; a benzoyl group and a tetrahydropyranyl group.

Here, the lower alkyl group of $R^1$ means a lower $C_{1-4}$ alkyl group and specific examples include methyl, ethyl, propyl, isopropyl, butyl, isobutyl and sec-butyl, with the ethyl being preferred.

Preferred specific examples of $R^1$ include 1-tert-butyldimethylsilyloxyethyl, 1-tert-butyldiphenylsilyloxyethyl, 1-triethylsilyloxyethyl, 1-triisopropylsilyloxyethyl, 1-trimethylsilyloxyethyl, 1-dimethylthexylsilyloxyethyl and 1-hydroxyethyl, of which the 1-tert-butyldimethylsilyloxyethyl is particularly preferred.

Examples of the eliminative group of Z include acyloxy groups (ex. alkanoyloxy, aroyloxy, arylalkanoyloxy, alkylsulfonyloxy, arylsulfonyloxy, alkoxycarbonyloxy, aralkoxycarbonyloxy, alkoxyalkanoyloxy and carbamoyloxy), thionyl groups (ex. alkanoylthio, aroylthio, alkylthio and arylthio), sulfinyl groups (ex. alkylsulfinyl and arylsulfinyl), sulfonyl groups (ex. alkylsulfonyl and arylsulfonyl) and halogen atoms.

When Z represents an alkanoyloxy group, specific examples of it include linear alkanoyloxy groups each of which may be substituted by a halogen atom or a cyano group, for example, acetoxy, propionyloxy, butyryloxy, α-fluoroacetoxy, α-chloroacetoxy, α-bromoacetoxy, α-iodoacetoxy, α,α-difluoroacetoxy, α,α-dichloroacetoxy and α-cyanoacetoxy, and branched or cyclic alkanoyloxy groups such as isobutyryloxy and cyclohexylcarbonyloxy.

When Z represents an aroyloxy group, specific examples of it include monocyclic or bicyclic aroyloxy groups which may contain a hetero atom, such as benzoyloxy, 1-naphthoyloxy, 2-naphthoyloxy, nicotinoyloxy, isonicotinoyloxy and flufuroyloxy.

When Z represents an arylalkanoyloxy group, specific examples include arylalkanoyloxy groups such as phenylacetoxy.

When Z represents an alkylsulfonyloxy group, specific examples include alkylsulfonyloxy groups such as methanesulfonyloxy, ethanesulfonyloxy, propanesulfonyloxy and trifluoromethanesulfonyloxy.

When Z represents an arylsulfonyloxy group, specific examples include arylsulfonyloxy groups such as benzenesulfonyloxy and toluenesulfonyloxy.

When Z represents an alkoxycarbonyloxy group, specific examples of it include alkoxycarbonyloxy groups such as methoxycarbonyloxy and ethoxycarbonyloxy.

When Z represents an aralkoxycarbonyloxy group, specific examples include aralkoxycarbonyloxy groups such as benzyloxycarbonyloxy.

When Z represents an alkoxyalkanoyloxy group, specific examples include alkoxyalkanoyloxy groups such as methoxyacetoxy and ethoxyacetoxy.

When Z represents a carbamoyloxy group, specific examples include carbamoyloxy groups such as N-methylcarbamoyloxy, N-ethylcarbamoyloxy and N-phenylcarbamoyloxy.

When Z represents an alkanoylthio group, specific examples include alkanoylthio groups such as acetylthio and propinylthio.

When Z represents an aroylthio group, specific examples include aroylthio groups such as benzoylthio.

When Z represents an alkylthio group, specific examples include alkylthio groups such as methylthio, ethylthio, propylthio, isopropylthio, butylthio, isobutylthio and tert-butylthio.

When Z represents an arylthio group, specific examples include arylthio groups such as phentylthio.

When Z represents an alkylsulfinyl group, specific examples include alkylsulfinyl groups such as methanesulfinyl, ethanesulfinyl, propanesulfinyl and butanesulfinyl.

When Z represents an arylsulfinyl group, specific examples include arylsulfinyl groups such as benzenesulfinyl and toluenesulfinyl.

When Z represents an alkylsulfonyl group, specific examples include alkylsulfonyl groups such as methanesulfonyl, ethanesulfonyl, propanesulfonyl and butanesulfonyl.

When Z represents an arylsulfonyl group, specific examples include arylsulfonyl groups such as benzenesulfonyl.

When Z represents a halogen atom, specific examples include halogen atoms such as fluorine, chlorine and bromine.

As the particularly preferred example of Z, an acetoxy group can be mentioned by way of example.

There is no particular limitation imposed on the preparation process of the azetidinone derivative of the formula (I). It can be prepared, for example, by the process as described in Shun-Ichi Murahashi, et al., *J. Am. Chem. Soc.*, 112, 7820–782:2(1990), Shun-Ichi Murahashi, et al., *Tetrahedron Letters*, 32, 2145–2148(1991), or Shun-Ichi Murahashi, et al., *Tetrahedron Letters*, 32, 5991–5994(1991) or in a similar manner thereto.

Specific examples of the azetidinone derivative of the formula (I) include the following compounds:

4-acetoxy-3-[1-tert-butyldimethylsilyloxyethyl]-azetidin-2-one, 4-acetoxy-3-[1-tert-butyldiphenylsilyloxyethyl]-azetidin-2-one, 4-acetoxy-3-[1-triethylsilyloxyethyl]-azetidin-2-one, 4-acetoxy-3-[1-trimethylsilyloxyethyl]-azetidin-2-one, 4-acetoxy-3-[1-dimethylthexylsilyloxyethyl]-azetidin-2-one, 4-acetoxy-3-[1-hydroxyethyl]-azetidin-2-one, 4-isobutyryloxy-3-[1-tert-butyldimethylsilyloxyethyl]-azetidin-2-one, 4-propionyloxy-3-[1-tert-butyldimethylsilyloxyethyl]-azetidin-2-one, and 4-benzoyloxy-3-[1-tert-butyldimethylsilyloxyethyl]-azetidin-2-one, of which the 4-acetoxy-3-[1-tert-butyldimethylsilyloxyethyl]-azetidin-2-one is preferred.

In the magnesium compound of the formula (III) in the present invention, $R^1$ represents (1) a $C_{1-12}$ alkyl group, (2) a $C_{2-4}$ alkenyl group, (3) a 5- to 8-membered alicyclic group which may be substituted by a lower $C_{1-4}$ alkyl group, (4) a phenyl group which may be substituted by a lower $C_{1-4}$ alkyl group, a lower $C_{1-4}$ alkoxy group or a halogen atom, or (5) a benzyl group which may be substituted by a lower $C_{1-4}$ alkyl group, a lower $C_{1-4}$ alkoxy group or a halogen atom. $R^6$ represents (1) a halogen atom, (2) a methanesulfonyloxy group, (3) a benzenesulfonyloxy group, (4) a p-toluenesulfonyloxy group, (5) a trifluoromethanesulfonyloxy group, (6) an acetoxy group which may be substituted by a halogen atom or a cyano group, or (7) an $OR^7$ group wherein $R^7$ represents a lower $C_{1-4}$ alkyl group, a substituted or unsubstituted phenyl group, or a substituted or unsubstituted benzyl group.

Here, specific examples of $R^5$ of the magnesium compound (III) include (1) $C_{1-12}$ alkyl groups such as methyl, ethyl, propyl, isopropyl, butyl, isobutyl, sec-butyl, tert-butyl, pentyl, hexyl, heptyl, octyl, nonyl, decyl, undecyl and dodecyl, (2) $C_{2-4}$ alkenyl groups such as vinyl, allyl, 1-propenyl, isopropenyl, 1-butenyl, 2-butenyl and 2-methylallyl, (3) 5- to 8-membered alicyclic groups, each of which may have a substituent, such as cyclopentyl, cyclohexyl, cycloheptyl and cyclooctyl (here, the substituent being a lower $C_{1-4}$ alkyl group such as methyl, ethyl, propyl, isopropyl, butyl, isobutyl, sec-butyl or tert-butyl), and (4), (5) phenyl groups each of which may have a substituent and benzyl groups each of which may have a substituent (here, the substituent being a lower $C_{1-4}$ alkyl group such as methyl, ethyl, propyl, isopropyl, butyl, isobutyl, sec-butyl or tert-butyl, a lower $C_{1-4}$ alkoxy group such as methoxy, ethoxy, propoxy, isopropoxy, butoxy, isobutoxy, sec-butoxy or tert-butoxy, or a halogen atom such as fluorine, chlorine, bromine or iodine).

Specific examples of $R^6$ include (1) halogen atoms such as fluorine, chlorine, bromine and iodine, (2) a methanesulfonyloxy group, (3) a benzenesulfonyloxy group, (4) a p-toluenesulfonyloxy group, (5) a trifluoromethanesulfonyloxy group, (6) acetoxy groups each of which may be substituted by a halogen atom or a cyano group (here, specific examples include α-fluoroacetoxy, α-chloroacetoxy, α-bromoacetoxy, α-iodoacetoxy, α, α-difluoroacetoxy, α,α-dichloroacetoxy and α-cyanoacetoxy), and (7) $OR^7$ groups (here, specific examples of $R^7$ include lower $C_{1-4}$ alkyl groups such as methyl, ethyl, propyl, isopropyl, butyl, isobutyl, sec-butyl and tert-butyl, substituted or unsubstituted phenyl groups and substituted or unsubstituted benzyl groups (the substituent being a lower $C_{1-4}$ alkyl group such as methyl, ethyl, propyl, isopropyl, butyl, isobutyl, sec-butyl or tert-butyl, a lower $C_{1-4}$ alkoxy group such as methoxy, ethoxy, propoxy, isopropoxy, butoxy, isobutoxy, sec-butoxy or tert-butoxy, or a halogen atom such as fluorine, chlorine, bromine or iodine).

Specific examples of the magnesium compound represented by the formula (III) include methylmagnesium chloride, methylmagnesium bromide, methylmagnesium iodide, methylmagnesium methanesulfonate, methylmagnesium p-toluenesulfonate, methylmagnesium methoxide, methylmagnesium ethoxide, methylmagnesium tert-butoxide, methylmagnesium phenoxide, ethylmagnesium chloride, ethylmagnesium bromide, ethylmagnesium iodide, ethylmagnesium methanesulfonate, ethylmagnesium p-toluenesulfonate, ethylmagnesium methoxide, ethylmagnesium ethoxide, ethylmagnesium tert-butoxide, ethylmagnesium phenoxide, propylmagnesium chloride, propylmagnesium bromide, propylmagnesium iodide, propylmagnesium methanesulfonate, propylmagnesium p-toluenesulfonate, propylmagnesium methoxide, propylmagnesium ethoxide, propylmagnesium tert-butoxide, propylmagnesium phenoxide, iso-propylmagnesium chloride, iso-propylmagnesium bromide, iso-propylmagnesium iodide, iso-propylmagnesium methanesulfonate, iso-propylmagnesium p-toluenesulfonate, iso-propylmagnesium methoxide, iso-propylmagnesium ethoxide, iso-propylmagnesiumn tert-butoxide, iso-propylmagnesium phenoxide, n-butylmagnesium chloride, n-butylmagnesium bromide, n-butylmagnesium iodide, n-butylmagnesium methanesulfonate, n-butylmagnesium p-toluenesulfonate, n-butylmagnesium methoxide, n-butylmagnesium ethoxide, n-butylmagnesium tert-butoxide, n-butylmagnesium phenoxide, iso-butylmagnesium chloride, iso-butylmagnesium bromide, iso-butylmagnesium iodide, iso-butylmagnesium methanesulfonate, iso-butylmagnesium p-toluenesulfonate, iso-butylmagnesium methoxide, iso-butylmagnesium ethoxide, iso-butylmagnesium tert-butoxide, iso-butylmagnesium phenoxide, sec-butylmagnesium chloride, sec-butylmagnesium bromide, sec-butylmagnesium iodide, sec-butylmagnesium methanesulfonate, sec-butylmagnesium p-toluenesulfonate, sec-butylmagnesium methoxide, sec-butylmagnesium ethoxide, sec-butylmagnesium tert-butoxide, sec-butylmagnesium phenoxide, tert-butylmagnesium chloride, tert-butylmagnesium bromide, tert-butylmagnesium iodide, tert-butylmagnesium methanesulfonate, tert-butylmagnesium p-toluenesulfonate, tert-butylmagnesium methoxide, tert-butylmagnesium ethoxide, tert-butylmagnesium tert-butoxide, tert-butylmagnesium phenoxide, cyclopentylmagnesium chloride, cyclopentylmagnesium bromide, cyclopentylmagnesium iodide, cyclopentylmagnesium methanesulfonate, cyclopentylmagnesium p-toluenesulfonate, cyclopentylmagnesium methoxide, cyclopentylmagnesium ethoxide, cyclopentylmagnesium tert-butoxide, cyclopentylmagnesium phenoxide, cyclohexylmagnesium chloride, cyclohexylmagnesium bromide, cyclohexylmagnesium iodide, cyclohexylmagnesium methanesulfonate, cyclohexylmagnesium p-toluenesulfonate, cyclohexylmagnesium methoxide, cyclohexylmagnesium ethoxide, cyclohexylmagnesium tert-butoxide, cyclohexylmagnesium phenoxide, phenylmagnesium chloride, phenylmagnesium bromide, phenylmagnesium iodide, phenylmagnesium methanesulfonate, phenylmagnesium p-toluenesulfonate, phenylmagnesium methoxide, phenylmagnesium ethoxide, phenylmagnesium tert-butoxide, phenylmagnesium phenoxide, p-tolylmagnesium chloride, p-tolylmagnesium bromide, p-tolylmagnesium iodide, p-tolylmagnesium methanesulfonate, p-tolylmagnesium p-toluenesulfonate, p-tolylmagnesium methoxide, p-tolylmagnesium ethoxide, p-tolylmagnesium tert-butoxide, p-tolylmagnesium phenoxide, benzylmagnesium chloride, benzylmagnesium bromide, benzylmagnesium iodide, benzylmagnesium methanesulfonate, benzylmagnesium p-toluenesulfonate, benzylmagnesium methoxide, benzylmagnesium ethoxide, benzylmagnesium tert-butoxide and benzylmagnesium phenoxide.

Preferred specific examples of the magnesium compound represented by the formula (III) include methylmagnesium chloride, methylmagnesium bromide, methylmagnesium iodide, methylmagnesium methanesulfonate, methylmagnesium tert-butoxide, ethylmagnesium chloride, ethylmagnesium bromide, ethylmagnesium iodide, ethylmagnesium methanesulfonate, ethylmagnesium tert-butoxide, propylmagnesium chloride, propylmagnesium bromide, propylmagnesium iodide, propylmagnesium methanesulfonate, propylmagnesium tert-butoxide, iso-propylmagnesium chloride, iso-propylmagnesium bromide, iso-propylmagnesium iodide, iso-propylmagnesium methanesulfonate, iso-propylmagnesium tert-butoxide, n-butylmagnesium chloride, n-butylmagnesium bromide, n-butylmagnesium iodide, n-butylmagnesium methanesulfonate, n-butylmagnesium tert-butoxide, sec-butylmagnesium chloride, sec-butylmagnesium bromide, sec-butylmagnesium iodide, sec-butylmagnesium methanesulfonate, sec-butylmagnesium tert-butoxide, iso-butylmagnesium chloride, iso-butylmagnesium bromide, iso-butylmagnesium iodide, iso-butylmagnesium methanesulfonate, iso-butylmagnesium tert-butoxide, tert-butylmagnesium chloride, tert-butylmagnesium bromide, tert-butylmagnesium iodide, tert-butylmagnesium methanesulfonate, tert-butylmagnesium tert-butoxide, phenylmagnesium chloride, phenylmagnesium bromide, phenylmagnesium iodide, phenylmagnesium methanesulfonate, phenylmagnesium tert-butoxide, p-tolylmagnesium chloride, p-tolylmagnesium bromide, p-tolylmagnesium iodide, p-tolylmagnesium methanesulfonate, p-tolylmagnesium tert-butoxide, benzylmagnesium chloride, benzylmagnesium bromide, benzylmagnesium iodide, benzylmagnesium methanesulfonate and benzylmagnesium tert-butoxide.

Although no particular limitation is imposed on the preparation process of the magnesium compound (III), it can be prepared, for example, by the process as described in D. A. Shirley, *Org. React.*, 8, 28–58(1954) or in a similar manner thereto. Alternatively, a commercially available product may be employed.

The amide compound in the present invention is represented by the following formula (II):

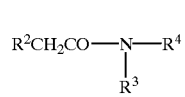

(II)

wherein, $R^2$ represents a hydrogen atom or a lower $C_{1-4}$ alkyl group, $R^3$ represents (1) a $C_{1-12}$ alkyl group, (2) a $C_{2-5}$ alkenyl group, (3) a $C_{1-6}$ organosilyl group, (4) a phenyl group which may be substituted by a lower $C_{1-4}$ alkyl group, a lower $C_{1-4}$ alkoxy group, a nitro group or a halogen atom, (5) a $C_{6-13}$ aralkyl group which may be substituted by a lower $C_{1-4}$ alkyl group, (6) a 5- to 8-membered alicyclic group which may be substituted by a lower $C_{1-4}$ alkyl group, or (7) a naphthyl group and $R^4$ represents an electron withdrawing group; or $R^3$ and $R^4$ may form a heterocycle together with the adjacent nitrogen atom.

Specific examples of $R^2$ of the amide compound (II) include a hydrogen atom and lower $C_{1-4}$ alkyl groups such as methyl, ethyl, propyl, isopropyl, butyl, isobutyl, sec-butyl and tert-butyl.

When $R^3$ of the amide compound (II) represents (1) a $C_{1-12}$ alkyl group, specific examples of it include methyl, ethyl, propyl, isopropyl, butyl, isobutyl, sec-butyl, tert-butyl, pentyl, hexyl, heptyl, octyl, nonyl, decyl, undecyl and dodecyl.

When $R^3$ represents (2) a $C_{2-5}$ alkenyl group, specific examples of it include vinyl, allyl, 1-propenyl, isopropenyl, 1-butenyl, 2-butenyl and 2-methylallyl.

When $R^3$ represents (3) a $C_{1-6}$ organosilyl group, specific examples include tert-butyldimethylsilyl, tert-butyldiphenylsilyl, triethylsilyl, dimethylcumylsilyl, triisopropylsilyl, dimethylhexylsilyl and dimethylthexylsilyl.

When $R^3$ represents (4) a phenyl group which may be substituted by a lower $C_{1-4}$ alkyl group, a lower $C_{1-4}$ alkoxy group, a nitro group or a halogen atom, specific examples of the substituent include lower $C_{1-4}$ alkyl groups such as methyl, ethyl, propyl, isopropyl, butyl, isobutyl, sec-butyl and tert-butyl, lower $C_{1-4}$ alkoxy groups such as methoxy, ethoxy, propoxy, isopropoxy, butoxy, isobutoxy, sec-butoxy and tert-butoxy, halogen atoms such as fluorine, chlorine, bromine and iodine and a nitro group.

When $R^3$ represents (5) a $C_{6-13}$ aralkyl group which may be substituted by a lower $C_{1-4}$ alkyl group, specific examples of it include $C_{6-13}$ aralkyl groups such as benzyl, α-phenylethyl, β-phenylethyl, α-phenylpropyl, β-phenylpropyl, γ-phenylpropyl and naphthylmethyl. Here, specific examples of the substituent include lower $C_{1-4}$ alkyl groups such as methyl, ethyl, propyl, isopropyl, butyl, isobutyl, sec-butyl and tert-butyl.

When $R^3$ represents (6) a 5- to 8-membered alicyclic group which may be substituted by a lower $C_{1-4}$ alkyl group, specific examples of it include 5- to 8-membered alicyclic groups such as cyclopentyl, cyclohexyl, cycloheptyl and cyclooctyl. Here, specific examples of the substituent include lower $C_{1-4}$ alkyl groups such as methyl, ethyl, propyl, isopropyl, butyl, isobutyl, sec-butyl and tert-butyl.

When $R^3$ represents (7) a naphthyl group, specific examples of it include a naphthyl group.

In the present invention, the amide compound represented by the formula (II) is a compound selected from the amide compounds represented by the following formulas (V), (VI) and (VII):

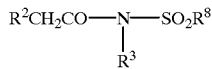
(V)

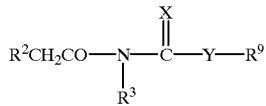
(VI)

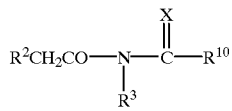
(VII)

wherein $R^2$ and $R^3$ have the same meanings as described above, X represents an oxygen atom, a sulfur atom or an $NR^{11}$ group wherein $R^{11}$ represents a substituted or unsubstituted alkyl group or a substituted or unsubstituted phenyl group, Y represents an oxygen atom or a sulfur atom, $R^8$, $R^9$ and $R^{10}$ each independently represents (1) a $C_{1-12}$ alkyl group, (2) a phenyl group which may be substituted by a lower $C_{1-4}$ alkyl group, a lower $C_{1-4}$ alkoxy group, a nitro group or a halogen atom, (3) a benzyl group which may be substituted by a lower $C_{1-4}$ alkyl group, (4) a 5- to 7-membered alicyclic group which may be substituted by a lower $C_{1-4}$ alkyl group or (5) a naphthyl group, or (6) may form a 4- to 6-membered ring together with $R^3$.

As $R^2$ and $R^3$ of the amide compound (V), (VI) or (VII), those exemplified above as $R^2$ and $R^3$ can be mentioned, respectively.

Specific examples of X of the amide compound (V), (VI) or (VII) include an oxygen atom, a sulfur atom and $NR^{11}$ groups (here, specific examples of $R^{11}$ include substituted or unsubstituted $C_{1-12}$ alkyl groups such as methyl, ethyl, propyl, isopropyl, butyl, isobutyl, sec-butyl, tert-butyl, pentyl, hexyl, heptyl, octyl, nonyl, decyl, undecyl and dodecyl (here, specific examples of the substituent include lower $C_{1-4}$ alkyl groups such as methyl, ethyl, propyl, isopropyl, butyl, isobutyl, sec-butyl and tert-butyl, lower $C_{1-4}$ alkoxy groups such as methoxy, ethoxy, propoxy, isopropoxy, butoxy, isobutoxy, sec-butoxy and tert-butoxy, halogen atoms such as fluorine, chlorine, bromine and iodine, and a nitro group), and substituted or unsubstituted phenyl groups (here, specific examples of the substituent include lower $C_{1-4}$ alkyl groups such as methyl, ethyl, propyl, isopropyl, butyl, isobutyl, sec-butyl and tert-butyl, lower $C_{1-4}$ alkoxy groups such as methoxy, ethoxy, propoxy, isopropoxy, butoxy, isobutoxy, sec-butoxy and tert-butoxy, halogen atoms such as fluorine, chlorine, bromine and iodine, and a nitro group).

In the amide compound (V), (VI) or (VII), Y represents an oxygen atom or a sulfur atom.

In the amide compound (V), (VI) or (VII), when $R^8$, $R^9$ or $R^{10}$ represents (1) a $C_{1-12}$ alkyl group, specific examples of it include methyl, ethyl, propyl, isopropyl, butyl, isobutyl, sec-butyl, tert-butyl, pentyl, hexyl, heptyl, octyl, nonyl, decyl, undecyl and dodecyl.

When $R^8$, $R^9$ or $R^{10}$ represents (2) a phenyl group which may be substituted by a lower $C_{1-4}$ alkyl group, a lower $C_{1-4}$ alkoxy group, a nitro group or a halogen atom, specific examples of the substituent include lower $C_{1-4}$ alkyl groups such as methyl, ethyl, propyl, isopropyl, butyl, isobutyl, sec-butyl and tert-butyl, lower $C_{1-4}$ alkoxy groups such as methoxy, ethoxy, propoxy, isopropoxy, butoxy, isobutoxy, sec-butoxy and tert-butoxy, halogen atoms such as fluorine, chlorine, bromine and iodine and a nitro group.

When $R^8$, $R^9$ or $R^{10}$ represents (3) a benzyl group which may be substituted by a lower $C_{1-4}$ alkyl group, specific examples of the substituent include lower $C_{1-4}$ alkyl groups such as methyl, ethyl, propyl, isopropyl, butyl, isobutyl, sec-butyl and tert-butyl.

When $R^8$, $R^9$ or $R^{10}$ represents (4) a 5- to 7-membered alicyclic group which may be substituted by a lower $C_{1-4}$ alkyl group, specific examples of it include 5- to 7-membered alicyclic groups such as cyclopentyl, cyclohexyl and cycloheptyl. Specific examples of the substituent include lower $C_{1-4}$ alkyl groups such as methyl, ethyl, propyl, isopropyl, butyl, isobutyl, sec-butyl and tert-butyl.

When $R^8$, $R^9$ or $R^{10}$ represents (5) a naphthyl group, specific examples of it include a naphthyl group.

$R^8$, $R^9$ or $R^{10}$ (6) may form a 4- to 6-membered ring together with $R^3$.

Although no particular limitation is imposed on the preparation process of the amide compound represented by the formula (V), (VI) or (VII), it can be synthesized, for example, by the process as described in WO93/13064 or in a similar manner thereto.

Specific examples of the amide compound of the formula (V) include following compounds:

N-cyclohexyl-N-p-toluenesulfonylpropionamide,
N-cyclopentyl-N-p-toluenesulfonylpropionamide,
N-isopropyl-N-p-toluenesulfonylpropionamide,
N-(tert-butyl)-N-p-toluenesulfonylpropionamide,
N-phenyl-N-p-toluenesulfonylpropionamide,
N-benzyl-N-p-toluenesulfonylpropionamide,
N-[(S)-phenethyl]-N-p-toluenesulfonylpropionamide,
N-[(R)-phenethyl]-N-p-toluenesulfonylpropionamide,
N-cyclohexyl-N-4-methoxybenzenesulfonylpropionamide,
N-cyclohexyl-N-4-tert-butylbenzenesulfonylpropionamide,
N-cyclohexyl-N-2-naphthalenesulfonylpropionamide,
N-cyclohexyl-N-4-bromobenzenesulfonylpropionamide and
N-(4-chlorophenyl)-N-p-toluenesulfonylpropionamide.

Specific examples of the amide compound of the formula (VI) include the following compounds:

methyl N-methyl-N-propionylcarbamate,
methyl N-methyl-N-propionylthiocarbamate,
methyl N-tert-butyl-N-propionylcarbamate,
methyl N-tert-butyl-N-propionylthiocarbamate,
methyl N-phenyl-N-propionylcarbamate and
methyl N-phenyl-N-propionylthiocarbamate.

Specific examples of the amide compound of the formula (VII) include the following compounds:

N-methyl-N-propionylbenzamide,
N-ethyl-N-propionylbenzamide,
N-isopropyl-N-propionylbenzamide and
N-phenyl-N-propionylbenzamide.

Furthermore, the amide compound of the formula (V) is a compound selected from the amide compounds represented by the following formulas (VIII), (IX), (X), (XI) and (XII):

$$R^2CH_2CO-N(SO_2)(R^{14})(R^{15})(R^{12})(R^{13})(W) \quad (VIII)$$

$$R^2CH_2CO-N(SO_2)(R^{14})(R^{15})(R^{12})(R^{13})(R^{16})(R^{17}) \quad (IX)$$

$$R^2CH_2CO-N(SO_2)(R^{14})(R^{15})(R^{16})(R^{12})(R^{13})(W)(R^{17}) \quad (X)$$

$$R^2CH_2CO-N(SO_2)(R^{14})(R^{15})(R^{12})(R^{13})(W)(R^{16})(R^{19}) \quad (XI)$$

$$R^2CH_2CO-N(SO_2)(R^{14})(R^{15})(R^{23})(R^{12})(R^{13})(R^{20})(R^{21})(R^{22}) \quad (XII)$$

wherein $R^2$ has the same meaning as described above, W represents an oxygen atom or a sulfur atom, and $R^{12}$ to $R^{23}$ are the same or different and each independently represents (1) a hydrogen atom, (2) a $C_{1-12}$ alkyl group, (3) a phenyl group which may be substituted by a lower $C_{1-4}$ alkyl group, a lower $C_{1-4}$ alkoxy group, a nitro group or a halogen atom, (4) a benzyl group which may be substituted by a lower $C_{1-4}$ alkyl group, (5) a 5- to 7-membered alicyclic group which may be substituted by a lower $C_{1-4}$ alkyl group, or (6) a naphthyl group; or (7) any two of $R^{12}$ to $R^{23}$ on the same carbon atom may be coupled together to form a $C_{4-6}$ alkylene group, (8) any two of $R^{12}$ to $R^{23}$ on the adjacent carbon atoms may form, together with the carbon atoms, an aromatic ring which may have a substituent wherein said substituent is a lower $C_{1-4}$ alkyl group, a lower $C_{1-4}$ alkoxy group, an aryl group, a hydroxyl group or a halogen atom, (9) any two of $R^{12}$ to $R^{23}$ on the adjacent carbon atoms may be coupled together to form a $C_{3-6}$ alkylene group, or (10) any two of $R^{12}$ to $R^{23}$ on the adjacent carbon atoms may form, together with the carbon atoms, a polycyclic group.

As $R^2$ of the amide compound (VIII), (IX), (X), (XI) or (XII), those exemplified above as $R^2$ can be mentioned.

Specific examples of W of the amide compound (VIII), (IX), (X), (XI) or (XII) include an oxygen atom and a sulfur atom.

Examples of $R^{12}$ to $R^{23}$ of the amide compound (VIII), (IX), (X), (XI) or (XII) include (1) a hydrogen atom.

Specific examples of (2) the $C_{1-12}$ alkyl group represented by $R^{12}$ to $R^{23}$ include those exemplified above with respect to $R^8$, $R^9$ or $R^{10}$.

Specific examples of (3) the phenyl group, as $R^{12}$ to $R^{23}$, which may be substituted by a lower $C_{1-4}$ alkyl group, a lower $C_{1-4}$ alkoxy group, a nitro group or a halogen atom include those exemplified above with respect to $R^8$, $R^9$ or $R^{10}$.

Specific examples of (4) the benzyl group, as $R^{12}$ to $R^{23}$, which may be substituted by a lower $C_{1-4}$ alkoxy group include those exemplified above with respect to $R^8$, $R^9$ or $R^{10}$.

Specific examples of (5) the 5- to 7-membered alicyclic group, as $R^{12}$ to $R^{23}$, which may be substituted by a lower $C_{1-4}$ alkyl group include those exemplified above with respect to $R^8$, $R^9$ or $R^{10}$.

Specific examples of (6) the naphthyl group include that exemplified above with respect to $R^8$, $R^9$ or $R^{10}$.

When in $R^{12}$ to $R^{23}$, (7) any two of $R^{12}$ to $R^{23}$ on the same carbon atom are coupled together to form a $C_{4-6}$ alkylene group, specific examples include $C_{4-7}$ alkylene groups such as 1,4-butylene, 1,5-pentylene, 1,6-hexylene and 1,7-heptylene. Specific examples of the substituent include lower $C_{1-4}$ alkyl groups such as methyl, ethyl, propyl, isopropyl, butyl, isobutyl, sec-butyl and tert-butyl.

When in $R^{12}$ to $R^{23}$, (8) any two of $R^{12}$ to $R^{23}$ on the adjacent carbon atoms form, together with the carbon atoms, an aromatic ring which may have a substituent wherein said substituent is a lower $C_{1-4}$ alkyl group, a lower $C_{1-4}$ alkoxy group, an aryl group, a hydroxyl group or a halogen atom, specific examples include aromatic rings which may have a substituent (here, specific examples of the substituent include lower $C_{1-4}$ alkyl groups such as methyl, ethyl, propyl, isopropyl, butyl, isobutyl, sec-butyl and tert-butyl, lower $C_{1-4}$ alkoxy groups such as methoxy, ethoxy, propoxy, isopropoxy, butoxy, isobutoxy, sec-butoxy and tert-butoxy, halogen atoms such as fluorine, chorine, bromine and iodine) such as benzene, naphthalene, phenanthrene, furan, thiophene, benzofuran, isobenzofuran, pyrrole, pyridine, pyrimidine, pyrazine, pyridazine, indole, isoindole, quinoline and isoquinoline rings.

When in $R^{12}$ to $R^{23}$, (9) any two of $R^{12}$ to $R^{23}$ on the adjacent carbon atoms are coupled together to form a $C_{3-6}$ alkylene group, specific examples include $C_{3-6}$ alkylene groups which may have a substituent (here, specific examples of the substituent include lower $C_{1-4}$ alkyl groups such as methyl, ethyl, propyl, isopropyl, butyl, isobutyl, sec-butyl and tert-butyl, lower $C_{1-4}$ alkoxy groups such as methoxy, ethoxy, propoxy, isopropoxy, butoxy, isobutoxy, sec-butoxy and tert-butoxy, halogen atoms such as fluorine, chorine, bromine and iodine and aryl groups) such as 1,3-propylene, 1,4-butylene, 1,5-pentylene and 1,6-hexylene.

When in $R^{12}$ to $R^{23}$, (10) any two of $R^{12}$ to $R^{23}$ on the adjacent carbon atoms form, together with the carbon atoms, a polycyclic group, specific examples include polycyclic groups which may have a substituent (here, specific examples of the substituent include lower $C_{1-4}$ alkyl groups such as methyl, ethyl, propyl, isopropyl, butyl, isobutyl, sec-butyl and tert-butyl, lower $C_{1-4}$ alkoxy groups such as methoxy, ethoxy, propoxy, isopropoxy, butoxy, isobutoxy, sec-butoxy and tert-butoxy, and halogen atoms such as fluorine, chorine, bromine and iodine) such as indane, norbornane and 1,2,3,4-tetrahydronaphthalene.

Although there is no particular limitation imposed on the preparation process of the amide compound of the formula (VIII), it can be synthesized, for example, by acylating the amine compound available by the process described in U.S. Pat. No. 3,345,374 in a known manner.

Specific examples of the amide compound of the formula (VIII) include N-propionyl-2-oxa-1,3-sultam and N-propionyl-1,2-benzisothiazole-2,3-dihydro-3-methyl-1,1-dioxide.

Although there is no particular limitation imposed on the preparation process of the amide compound of the formula (IX), it can be synthesized, for example, by the process described in Wolfgang Oppolzer, et al., *Tetrahedron Letters*, 31, 4117(1990) or in a similar manner thereto.

Specific examples of the amide compound of the formula (IX) include N-propionyl-bornane-10,2-sultam.

Although no particular limitation is imposed on the preparation process of the amide compound of the formula (X), it can be synthesized, for example, by ketalizing phenol-2-sulfonamide available by the process described in Peter F. Drygala, et al., *Synthetic Communications*, 24, 4117(1994) in a conventional manner and then acylating the resulting amide compound in a known manner.

Specific examples of the amide compound of the formula (X) include N-propionyl-4,1,2-benzoxathiazine-2,3-dihydro-3-methyl-1,1-dioxide.

Although no particular limitation is imposed on the preparation process of the amide compound of the formula (XI), it can be synthesized, for example, by acylating in a known manner the amine compound available by the process described in WO9205164.

Specific examples of the amide compound of the formula (XI) include N-propionyl-1H-4,2,1-benzoxathiazine-2,2-dioxide.

Although there is no particular limitation imposed on the preparation process of the amide compound of the formula (XII), it can be synthesized, for example, by acylating in a known manner the amine compound available by the process described in U.S. Pat. No. 3,303,189.

Specific examples of the amide compound of the formula (XII) include N-propionyl-2,1-benzothiazine-2,2-dioxide.

Furthermore, in the present invention, the amide compound of the formula (VI) is a compound selected from the amide compounds represented by the formula (XIII), (XIV) and (XV):

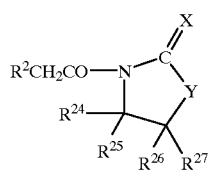

(XIII)

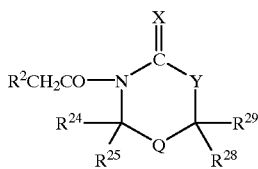

(XIV)

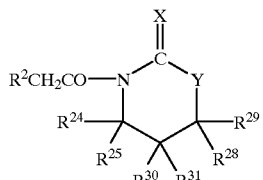

(XV)

wherein $R^2$, X and Y have the same meanings as described above, Q represents an oxygen atom or a sulfur atom, and $R^{24}$ to $R^{31}$ are the same or different and each independently represents (1) a hydrogen atom, (2) a $C_{1-12}$ alkyl group, (3) a phenyl group which may be substituted by a lower $C_{1-4}$ alkyl group, a lower $C_{1-4}$ alkoxy group, a nitro group or a halogen atom, (4) a benzyl group which may be substituted by a lower $C_{1-4}$ alkyl group, (5) a 5- to 7-membered alicyclic group which may be substituted by a lower $C_{1-4}$ alkyl group, or (6) a naphthyl group; or (7) any two of $R^{24}$ to $R^{31}$ on the same carbon atom may be coupled together to form a $C_{4-6}$ alkylene group, (8) any two of $R^{24}$ to $R^{31}$ on the adjacent carbon atoms may form, together with the carbon atoms, an aromatic ring which may have a substituent wherein said substituent is a lower $C_{1-4}$ alkyl group, a lower $C_{1-4}$ alkoxy group, an aryl group, a hydroxyl group or a halogen atom, (9) any two of $R^{24}$ to $R^{31}$ on the adjacent carbon atoms may be coupled together to form a $C_{3-6}$ alkylene group, or (10) any two of $R^{24}$ to $R^{31}$ on the adjacent carbon atoms may form, together with the carbon atoms, a polycyclic group.

As $R^2$, X and Y of the amide compound (XIII), (XIV) or (XV), those exemplified above as $R^2$, X and Y can be mentioned, respectively.

As Q of the amide compound (XIV), those exemplified above as W can be mentioned.

As $R^{24}$ to $R^{31}$ of the amide compound (XIII), (XIV) or (XV), those exemplified above with respect to $R^{12}$ to $R^{23}$ can be mentioned.

Although no particular limitation is imposed on the preparation process of the amide compound of the formula (XIII), it can be synthesized by the process described in, for example, JP-A-63-10765, JP-A-62-252786, JP-A-63-284176, JP-A-2-292269, JP-A-2-788, JP-A-61-275267, JP-A-62-169781, JP-A-62-77384, JP-A-63-170377, JP-A-62-246550 or JP-A-6-65195 or in a similar manner thereto.

Specific examples of the amide compound of the formula (XIII) include 4-methyl-3-propionyloxazolidin-2-one, 4,4-dimethyl-3-propionyloxazolidin-2-one, 4-phenyl-3-propionyloxazolidin-2-one, 4-benzyl-3-propionyloxazolidin-2-one, 4-isopropyl-3-propionyloxazolidin-2-one, 3-propionyl-(3aS-cis)-3,3a,8,tetrahydro-2H-indeno[1,2-d]oxazol-2-one and 3-propionyl-(3aR-cis)-3,3a,8,tetrahydro-2H-indeno[1,2-d]oxazol-2-one.

Although no particular limitation is imposed on the preparation process of the amide compound of the formula (XIV) or (XV), it can be synthesized, for example, by the process described in Malcom R. banks, et al., *Tetrahedron*, 48, 7979(1992) or in a similar manner thereto.

Specific examples of the amide compound of the formula (XIV) include N-propionyl-tetrahydro-1,5,3-dioxazin-2-one.

Specific examples of the amide compound of the formula (XV) include N-propionyl-4,4-dimethyl-tetrahydro-1,3-oxazin-2-one and N-propionyl-tetrahydro-1,3-oxazin-2-one-4,4-dimethyl.

Furthermore, in the present invention, the amide compound represented by the formula (VII) is a compound selected from the amide compounds represented by the following formulas (XVI), (XVII), (XVIII), (XIX), (XX) and (XXI):

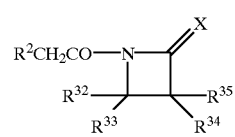

(XVI)

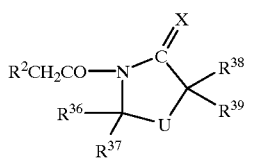

(XVII)

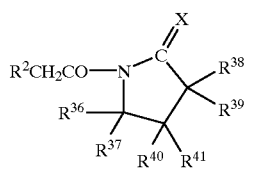

(XVIII)

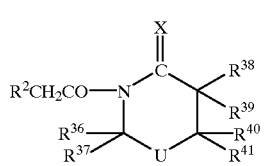

(XIX)

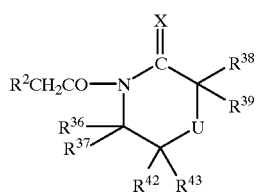

(XX)

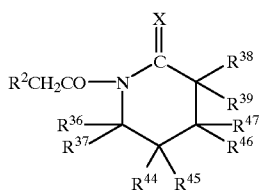

(XXI)

wherein $R^2$ and X have the same meanings as described above, U represents an oxygen atom or a sulfur atom, and $R^{32}$ to $R^{47}$ are the same or different and each independently represents (1) a hydrogen atom, (2) a $C_{1-12}$ alkyl group, (3) a phenyl group which may be substituted by a lower $C_{1-4}$ alkyl group, a lower $C_{1-4}$ alkoxy group, a nitro atom or a halogen atom, (4) a benzyl group which may be substituted by a lower $C_{1-4}$ alkyl group, (5) a 5- to 7-membered alicyclic group which may be substituted by a lower $C_{1-4}$ alkyl group or (6) a naphthyl group; or (7) any two of $R^{32}$ to $R^{47}$ on the same carbon atom may be coupled together to form a $C_{4-6}$ alkylene group, (8) any two of $R^{32}$ to $R^{47}$ on the adjacent carbon atoms may form, together with the carbon atoms, an aromatic ring which may have a substituent wherein said substituent is a lower $C_{1-4}$ alkyl group, a lower $C_{1-4}$ alkoxy group, an aryl group, a hydroxyl group or a halogen atom, (9) any two of $R^{32}$ to $R^{47}$ on the adjacent carbon atoms may be coupled together to form a $C_{3-6}$ alkylene group, or (10) any two of $R^{32}$ to $R^{47}$ on the adjacent carbon atoms may form, together with the carbon atoms, a polycyclic group.

As $R^2$ and X of the amide compound (XVI), (XVII), (XVIII), (XIX), (XX) or (XXI), those exemplified above as $R^2$ and X can be mentioned, respectively.

As U of the amide compound (XVI), (XVII), (XVIII), (XIX), (XX) or (XXI), those exemplified above as W can be mentioned.

As $R^{32}$ to $R^{47}$ of the amide compound (XVI), (XVII), (XVIII), (XIX), (XX) or (XXI), those exemplified above with respect to $R^{12}$ to $R^{23}$ can be mentioned.

Although no particular limitation is imposed on the preparation process of the amide compound of the formula (XVI), it can be synthesized by acylating a commercially available amine compound in a known manner.

Specific examples of the amide compound of the formula (XVI) include N-propionyl-3,3,4,4-tetramethylazetidin-2-one and N-propionyl-azetidin-2-one.

Although no particular limitation is imposed on the preparation process of the amide compound of the formula (XVII), it can be synthesized by acylating a commercially available amine compound in a known manner.

Specific examples of the amide compound of the formula (XVII) include 5,5-dimethyl-3-propionyl-2,2-pentamethyleneoxazolidin-4-one, 2,2-dibenzyl-5,5-dimethyl-3-propionyloxazolin-4-one.

Although no particular limitation is imposed on the preparation process of the amide compound of the formula (XVIII), it can be synthesized, for example, by the process described in JP-A-6-65195 or in a similar manner thereto.

Specific examples of the amide compound of the formula (XVIII) include 1-propionyl-5,5-dimethylpyrrolidin-2-one, 1-propionyl-5,5-diethylpyrrolidin-2-one, 1-propionyl-5,5-diisopropylpyrrolidin-2-one.

Although no particular limitation is imposed on the preparation process of the amide compound of the formula (XIX), it can be synthesized, for example, by the process described in JP-A-7-70116, JP-A-7-97381 or JP-A-7-165760, or in a similar manner thereto.

Specific examples of the amide compound of the formula (XIX) include 5,5-dimethyl-3-propionyl-2,2-pentamethyleneoxazin-4-one, 3-propionyl-spiro[2,3-dihydro-4H-1,3-benzoxazin-2,1'-cyclohexan]-4-one, 3-propionyl-spiro[2,3-dihydro-4H-1,3-naphthoxazine-2,1'-cyclohexan]-4-one.

Although no particular limitation is imposed on the amide compound of the formula (XX), it can be synthesized, for example, by acylating, in a known manner, an amine compound available by the process described in JP-A-63-295567 or in a similar manner thereto.

Specific examples of the amide compound of the formula (XX) include N-propionyl-3,4-dihydro-2H-1,4-benzoxazin-3-one.

Although no particular limitation is imposed on the preparation process of the amide compound of the formula (XXI), it can be synthesized., for example, by the process described in JP-A-7-97381 or in a similar manner thereto.

Specific examples of the amide compound of the formula (XXI) include N-propionyl-4H-isoquinolizin-1-one.

Although no particular limitation is imposed on the process for synthesizing the amide compound of the formula (II) from an amine compound, it can be synthesized by the process described in JP-A-7-97381 or in a similar manner thereto.

For example, the amide compound represented by the formula (II) can be prepared by reacting a compound represented by the following formula (IIa):

wherein $R^3$ and $R^4$ have the same meanings as described above with a compound of the following formula (IIb):

wherein $R^2$ has the same meaning as described above or a reactive derivative thereof.

The reaction of the compound (IIa) with the compound (IIb) can be carried out in a proper solvent in the presence of a dehydrating agent. Examples of the dehydrating agent include carbonyldiimidazole dicyclohexylcarbodiimide, N-hydroxysuccinimide and 1-hydroxybenzothiazole. Preferred examples of the solvent include diethyl ether, methylene chloride, tetrahydrofuran and acetonitrile. This reaction is carried out at a temperature of −30 to 70° C., preferably 0 to 30° C.

The reaction of the compound (IIa) with a reactive derivative of the compound (IIb) can be carried out in a proper solvent in the presence or absence of a base. As the reactive derivative, acid halides and acid anhydrides can be employed suitably. Examples of the base include alkali metal hydrides, alkali metals, lower alkyl and aryl lithium compounds, and organic bases such as pyridine, di(lower alkyl)anilines and tri(lower alkyl)amines. Preferred examples of the solvent include tetrahydrofuran, diethyl ether, benzene, toluene, methylene chloride and chloroform. This reaction is usually carried out at −80 to 50° C., preferably −20 to 30° C.

The preparation process according to the present invention will hereinafter be described specifically.

The preparation process of the present invention can be carried out reacting an amide compound of the formula (II) with a magnesium compound of the formula (III) in an organic solvent in an inert gas atmosphere such as argon or nitrogen, thereby producing the corresponding enolate (IIc) and then reacting the enolate (IIc) with an azetidinone compound of the formula (I), whereby a 4-substituted azetidinone compound of the formula (IV) can be prepared.

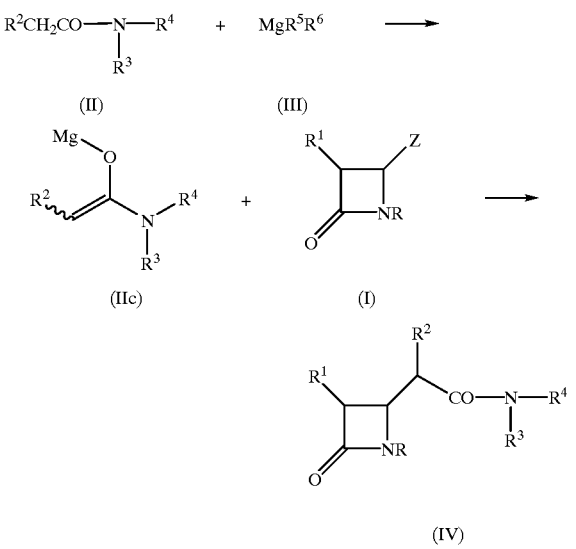

wherein R, $R^1$, $R^2$, $R^3$, $R^4$, $R^5$, $R^6$ and Z have the same meaning as described above.

As the solvent, inert solvents which do not take part in the reaction can be employed. Preferred examples include organic solvents, for example, hydrocarbon solvents such as pentane, hexane and heptane, chlorine solvents such as methylene chloride and chloroform, aromatic solvents such as benzene, chlorobenzene, toluene and xylene, and ether solvents such as diethyl ether, diisopropyl ether, tetrahydrofuran, dimethoxyethane, 1,3-dioxolane and dioxane; mixtures thereof.

Concerning the reaction temperature, the reaction for the preparation of the enolate (IIc) and the reaction of the enolate (IIc) with the azetidinone derivative (I) are each carried out at −50 to 100° C., preferably −20 to 50° C.

Concerning the reaction time, the reaction for the preparation of the enolate (IIc) and the reaction of the enolate (IIc) with the azetidinone derivative (I) are each carried out for 10 to 180 minutes, preferably 30 to 90 minutes.

Concerning the molar ratio, the amide compound of the formula (II) and the magnesium compound of the formula (III) are used each in an amount of 1 to 8 moles relative to 1 mole of the azetidinone derivative of the formula (I).

More preferably, the amide compound of the formula (II) and the magnesium compound of the formula (III) are used in amounts of 1 to 3 moles and 1 to 4 moles, respectively, relative to 1 mole of the azetidinone derivative of the formula (I).

When $R^2$ represents an alkyl group such as methyl, the α-form and the β-form so prepared differ in the ratio, depending on the kind of the amide compound of the formula (II), the kind of the magnesium compound of the formula (III), or the molar ratio. After the completion of the reaction, the desired product can be isolated by the ordinary post treatment.

It is also possible to subject the compound of the formula (IV) available by the preparation process of the present invention to hydrolysis after isolation or without isolation, thereby introducing into the corresponding carboxylic acid derivative represented by the formula (I'):

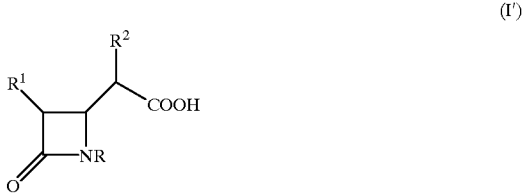

wherein R, $R^1$ and $R^2$ have the same meanings as described above.

EXAMPLES

The present invention will hereinafter be described more specifically by examples. It should however be borne in mind that the present invention is not limited by them and may be changed within an extent not departing from the scope of the present invention.

Apparatuses used for the measurement of various physical properties in each example are as follows:

Melting point measuring apparatus: "MP-500D" (product of Yanako Kiki Kaihatsu Kenkyujo)

$^1$H nuclear magnetic resonance spectrum ($^1$H-NMR): "AM-400" (400 MHz, product of Bruker Instruments Inc.), "Gemini-2000" (200 MHz, product of Varian, Inc.)

Internal standard substance: tetramethylsilane (in $CDCl_3$).

Abbreviations in each example are as follows:

TBDMSO: tert-butyldimethylsilyloxy group

OAc: acetoxy group.

Example 1

Preparation of 3-{(2R)-2-[(3S,4R)-3-[(1R)-1-tert-butyldimethylsilyloxyethyl]-2-oxoazetidin-4-yl]propionyl}-5,5-dimethyl-2,2-pentamethyleneoxazolin-4-one

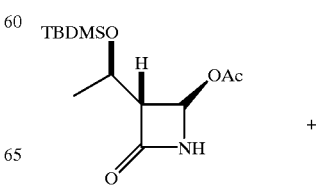

+

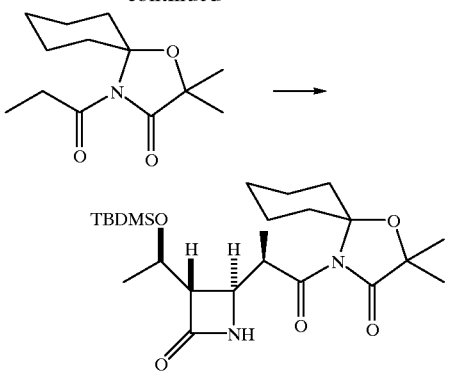

Under a nitrogen atmosphere, 2.22 ml (2.2 mmol) of a 0.99M tetrahydrofuran solution of sec-butylmagnesium chloride was added to a solution of 239 mg (1.0 mmol) of 5,5-dimethyl-3-propionyl-2,2-pentamethyleneoxazolidin-4-one in 2 ml of toluene at room temperature, followed by stirring at room temperature for 60 minutes. After cooling to 5° C., a solution of 287 mg (1.0 mmol) of (3R,4R)-4-acetoxy-3-[(R)-1-tert-butyldimethylsilyloxyethyl]-azetidin-2-one in 2 ml of toluene was slowly added dropwise, and the reaction mixture was stirred for further 10 minutes. Then, 2 ml of 2N-hydrochloric acid was added, followed by extraction with 10 ml of ethyl acetate. The organic layer was washed with 2 ml of a saturated aqueous solution of sodium bicarbonate, dried over anhydrous magnesium sulfate and distilled to remove the solvent. The residue was purified by column chromatography, whereby 289 mg (0.62 mmol) of a condensation product was obtained (yield: 62%, β:α= 79:21).

Examples 2 to 15 and Comparative Examples 1 and 2

In Examples 2 to 15, 5,5-dimethyl-2,2-pentamethylene-3-propionyloxazolidin-4-one and (3R,4R)-4-acetoxy-3-[(R)-1-tert-butyldimethylsilyloxyethyl]-azetidin-2-one were treated in a similar manner to Example 1 except for the use of the magnesium compounds (2.2 equivalents) shown in Table 1, respectively, whereby the title compound of Example 1 was obtained.

In Comparative Example 1 and Comparative Example 2, on the other hand, 5,5-dimethyl-2,2-pentamethylene-3-propionyloxazolidin-4-one and (3R,4R)-4-acetoxy-3-[(R)-1-tert-butyldimethylsilyloxyethyl]-azetidin-2-one were treated in a similar manner to Example 1 except for the respective use of the lithium compound and sodium compound shown in Table 1.

(In Table 1, Pr means a propyl group, Bu a butyl group, Bn a benzyl group, Ph a phenyl group and p-Tol a p-tolyl group.)

TABLE 1

| Example | Magnesium compound | β-methyl form:α-methyl form | Yield (%) |
|---|---|---|---|
| 2 | CH₃MgCl | 68:32 | 58 |
| 3 | C₂H₅MgCl | 75:25 | 52 |
| 4 | n-PrMgCl | 76:24 | 49 |
| 5 | iso-PrMgCl | 78:22 | 58 |
| 6 | n-BuMgCl | 79:21 | 56 |
| 7 | n-BuMgBr | 79:21 | 56 |
| 8 | n-BuMgI | 79:21 | 48 |
| 9 | n-BuMgOSO₂CH₃ | 72:28 | 49 |
| 10 | n-BuMgO-t-Bu | 74:26 | 50 |
| 11 | iso-BuMgCl | 79:21 | 60 |
| 12 | tert-BuMgCl | 79:21 | 59 |
| 13 | PhMgBr | 75:25 | 55 |
| 14 | p-TolMgCl | 78:22 | 54 |
| 15 | BnMgCl | 77:23 | 55 |
| Comp. Ex. 1 | iso-Pr₂NLi | — | 0 |
| Comp. Ex. 2 | [(CH₃)₃Si]₂NNa | — | 0 |

As is apparent from Example 1 and Table 1, the target compound could be obtained at a desirable yield in Examples 1 to 15 wherein the magnesium compound was employed, while in Comparative Example 1 wherein the lithium compound was employed and Comparative Example 2 wherein the sodium compound was employed, the target compound could not be obtained.

Example 16

Preparation of 3-{(2R)-2-[(3S,4R)-[(1R)-1-tert-butyldimethylsilyloxyethyl]-2-oxoazetidin-4-yl]propionyl}-2,2-dibenzyl-5,5-dimethyloxazolin-4-one

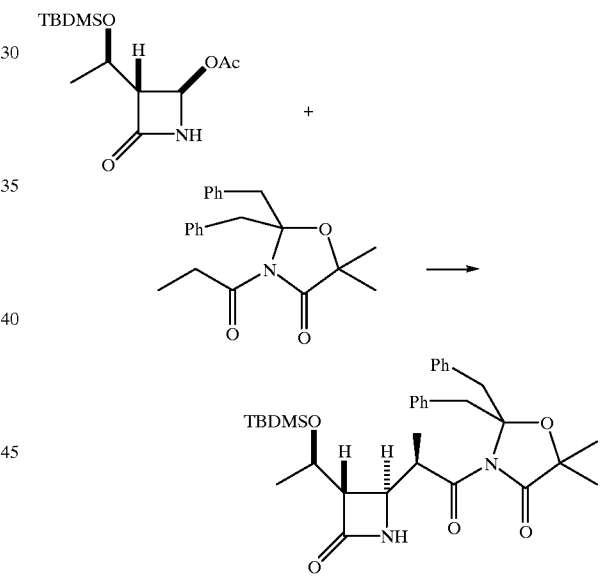

Under a nitrogen atmosphere, 2.22 ml (2.2 mmol) of a 0.99M tetrahydrofuran solution of sec-butylmagnesium chloride was added to a solution of 351 mg (1.0 mmol) of 2,2-dibenzyl-5,5-dimethyl-3-propionyloxazolin-4-one in 3 ml of toluene at room temperature, followed by stirring at room temperature for 60 minutes. After cooling to 5° C., a solution of 287 mg (1.0 mmol) of (3R,4R)-4-acetoxy-3-[(R)-1-tert-butyldimethylsilyloxyethyl]-azetidin-2-one in 2 ml of toluene was slowly added dropwise, and the reaction mixture was stirred for further 10 minutes. Then, 2 ml of 2N-hydrochloric acid was added, followed by extraction with 10 ml of ethyl acetate. The organic layer was washed with 2 ml of a saturated aqueous solution of sodium bicarbonate, dried over anhydrous magnesium sulfate and distilled to remove the solvent. The residue was purified by column chromatography, whereby 266 mg (0.46 mmol) of a condensation product was obtained (yield: 46%, β:α= 68:32).

Example 17

Preparation of 3-{(2R)-2-[(3S,4R)-3-[(1R)-1-tert-butyldimethylsilyloxyethyl]-2-oxoazetidin-4-yl]propionyl}-4,4-dimethyloxazolin-4-one

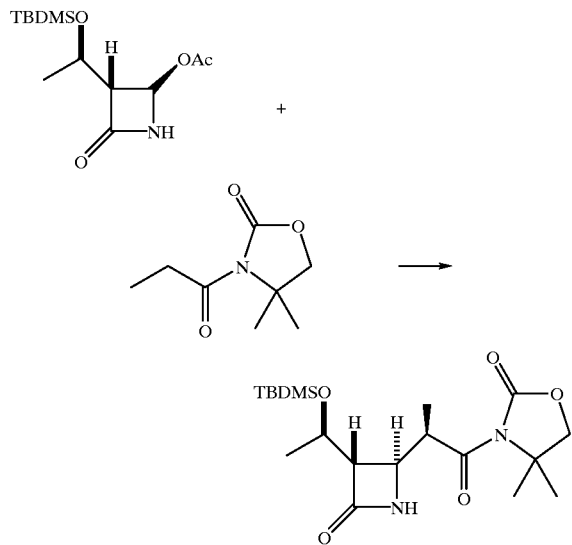

Under a nitrogen atmosphere, 18.3 ml (11 mmol) of a 0.60M tetrahydrofuran solution of t-butylmagnesium chloride was added to a solution of 1.80 g (10 mmol) of 4,4-dimethyl-3-propionyloxazolidin-2-one in 10 ml of tetrahydrofuran at room temperature, followed by heating to 50° C. After stirring for 30 minutes, the reaction mixture was cooled to 0° C. and then, was slowly added dropwise with a solution of 2.87 g (10 mmol) of (3R,4R)-4-acetoxy-3-[(R)-1-tert-butyldimethylsilyloxyethyl]-azetidin-2-one in 15 ml of tetrahydrofuran. The resulting mixture was stirred for further 30 minutes. Then, 40 ml of 2N-hydrochloric acid was added, followed by extraction with 40 ml of ethyl acetate. The organic layer was washed with 40 ml of a saturated aqueous solution of sodium bicarbonate, dried over anhydrous magnesium sulfate and distilled to remove the solvent. The residue was purified by column chromatography, whereby 2.38 g (6.0 mmol) of a condensation product was obtained (yield: 60%, β:α=60:40).

Example 18

Preparation of 3-{(2R)-2-[(3S,4R)-3-[(1R)-1-tert-butyldimethylsilyloxyethyl]-2-oxoazetidin-4-yl]propionyl}-(4S)-4-phenyloxazolin-4-one

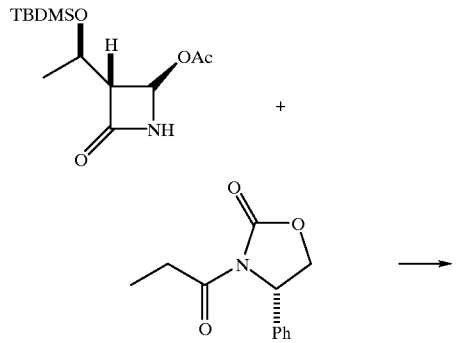

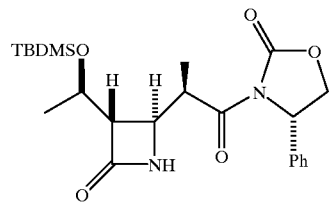

Under a nitrogen atmosphere, 2.44 ml (2.2 mmol) of a 0.90M tetrahydrofuran solution of t-butylmagnesium chloride was added to a solution of 219 mg (1.0 mmol) of (4S)-4-phenyl-3-propionyloxazolin-2-one in 2 ml of tetrahydrofuran at room temperature, followed by heating to 50° C. After stirring for 35 minutes, the reaction mixture was cooled to 5° C. and then, slowly added dropwise with a solution of 287 mg (1.0 mmol) of (3R,4R)-4-acetoxy-3-[(R)-1-tert-butyldimethylsilyloxyethyl]-azetidin-2-one in 2 ml of tetrahydrofuran. The resulting mixture was stirred for further 10 minutes. Then, 2 ml of 2N-hydrochloric acid was added, followed by extraction with 10 ml of ethyl acetate. The organic layer was washed with 2 ml of a saturated aqueous solution of sodium bicarbonate, dried over anhydrous magnesium sulfate and distilled to remove the solvent. The residue was purified by column chromatography, whereby 262 mg (0.59 mmol) of a condensation product was obtained (yield: 59%, β:α=96:4).

Example 19

Preparation of 3-{(2R)-2-[(3S,4R)-3-[(1R)-1-tert-butyldimethylsilyloxyethyl]-2-oxoazetidin-4-yl]propionyl}-4(S)-4-benzyloxazolin-4-one

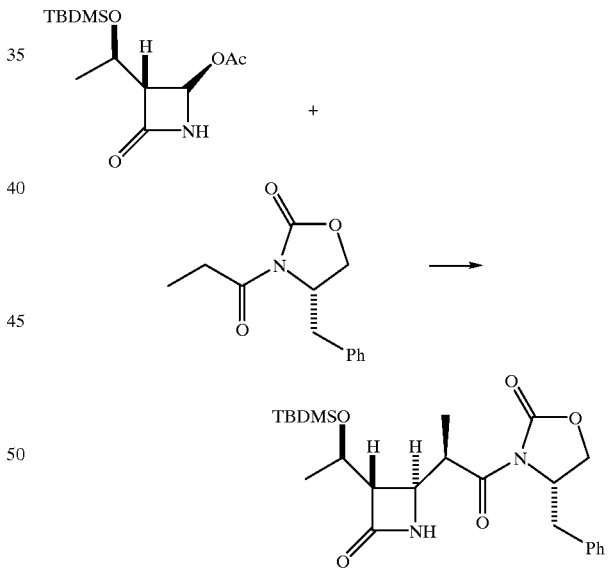

Under a nitrogen atmosphere, 2.44 ml (2.2 mmol) of a 0.90M tetrahydrofuran solution of t-butylmagnesium chloride was added to a solution of 233 mg (1.0 mmol) of 4(S)-4-benzyl-3-propionyloxazolin-2-one in 2 ml of tetrahydrofuran at room temperature, followed by heating to 50° C. After stirring for 35 minutes, the reaction mixture was cooled to 5° C. and then, slowly added dropwise with a solution of 287 mg (1.0 mmol) of (3R,4R)-4-acetoxy-3-[(R)-1-tert-butyldimethylsilyloxyethyl]-azetidin-2-one in 2 ml of tetrahydrofuran. The resulting mixture was stirred for further 10 minutes. Then, 2 ml of 2N-hydrochloric acid was added, followed by extraction with 10 ml of ethyl acetate.

The organic layer was washed with 2 ml of a saturated aqueous solution of sodium bicarbonate, dried over anhydrous magnesium sulfate and distilled to remove the solvent. The residue was purified by column chromatography, whereby 138 mg (0.30 mmol) of a condensation product was obtained (yield: 30%, β:α=86:14).

Example 20

Preparation of 3-{(2R)-2-[(3S,4R)-3-[(1R)-1-tert-butyldimethylsilyloxyethyl]-2-oxoazetidin-4-yl]propionyl}-4(S)-isopropyloxazolin-4-one

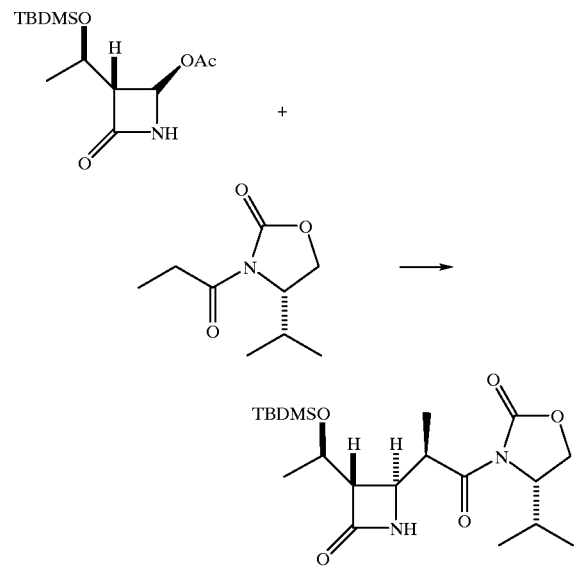

Under a nitrogen atmosphere, 1.5 ml (1.2 mmol) of a 0.80M tetrahydrofuran solution of t-butylmagnesium chloride was added to a solution of 203 mg (1.0 mmol) of 4(S)-4-isopropyl-3-propionyloxazolin-2-one at room temperature, followed by stirring at room temperature for 60 minutes. After cooling to 5° C., a solution of 287 mg (1.0 mmol) of (3R,4R)-4-acetoxy-3-[(R)-1-tert-butyldimethylsilyloxyethyl]-azetidin-2-one was slowly added dropwise. The resulting mixture was stirred for further 10 minutes. Then, 2 ml of 2N-hydrochloric acid was added, followed by extraction with 10 ml of ethyl acetate. The organic layer was washed with 2 ml of a saturated aqueous solution of sodium bicarbonate, dried over anhydrous magnesium sulfate and distilled to remove the solvent. The residue was purified by column chromatography, whereby 87 mg (0.21 mmol) of a condensation product was obtained (yield: 21%, β:α=78:22).

Example 21

Preparation of 3-{(2R)-2-[(3S,4R)-3-[(1R)-1-t-butyldimethylsilyloxyethyl]-2-oxoazetidin-4-yl]propionyl}-(3aS-cis)-3,3a,8,8a-tetrahydro-2H-indeno[1,2-d]oxazol-2-one

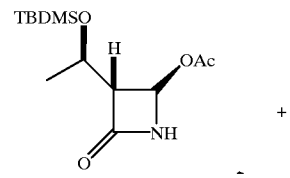

+

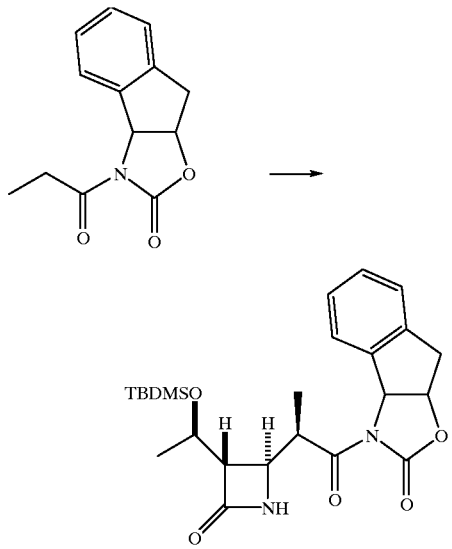

Under a nitrogen atmosphere, 231 mg (1.0 mmol) of 3-propionyl-(3aS-cis)-3,3a,8,8a-tetrahydro-2H-indeno[1,2-d]oxazol-2-one was charged in a 30-ml three-necked flask to dissolve it in 2 ml of tetrahydrofuran. To the resulting solution, 2.75 ml (2.2 mmol) of a tetrahydrofuran solution (0.8M) of t-butylmagnesium chloride was slowly added dropwise at room temperature. After the resulting mixture was allowed to react for 20 minutes under the same conditions, the reaction mixture was cooled to 5° C. and added with 2 ml of a tetrahydrofuran solution of 287 mg (1.0 mmol) of (3R,4R)-4-acetoxy-3-[(R)-1-tert-butyldimethylsilyloxyethyl]azetidin-2-one at the same temperature. After stirring for 10 minutes, 10 ml of ethyl acetate was added to the reaction mixture, followed by the dropwise addition of 2 ml of a 10% aqueous solution of citric acid. After separation, the organic layer was washed with 2 ml of a saturated aqueous solution of sodium bicarbonate and 2 ml of a saturated aqueous solution of sodium cloride, dried over anhydrous magnesium sulfate and distilled to remove the solvent. The residue was purified by column chromatography, whereby 308 mg (0.67 mmol) of a condensation product was obtained (yield: 67%, β:α=95:5).

Example 22

Preparation of 3-{(2R)-2-[(3S,4R)-3-[(1R)-1-t-butyldimethylsilyloxyethyl]-2-oxoazetidin-4-yl]propionyl}-(3aR-cis)-3,3a,8,8a-tetrahydro-2H-indeno[1,2-d]oxazol-2-one

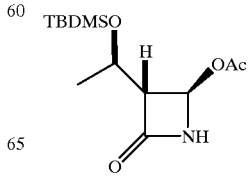

+

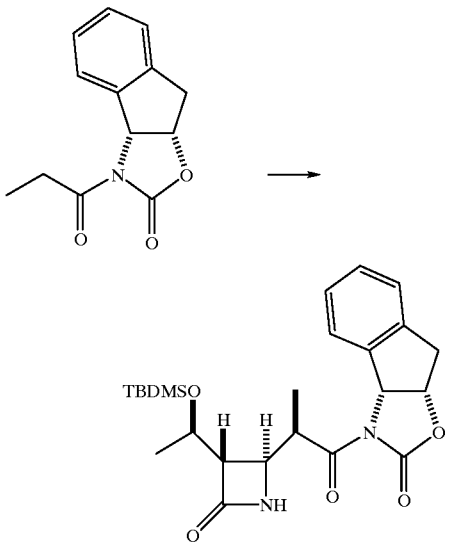

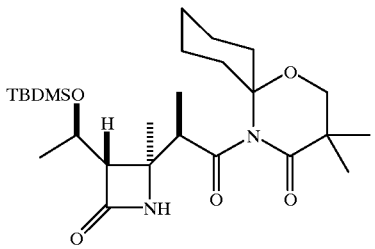

Under a nitrogen atmosphere, 231 mg (1.0 mmol) of 3-propionyl-(3aR-cis)-3,3a,8,8a-tetrahydro-2H-indeno[1,2-d]oxazol-2-one was charged in a 30-ml three-necked flask to dissolve it in 2 ml of tetrahydrofuran. To the resulting solution, 2.75 ml (2.2 mmol) of a tetrahydrofuran solution (0.8M) of t-butylmagnesium chloride was slowly added dropwise at room temperature. After the resulting mixture was allowed to react for 20 minutes under the same conditions, the reaction mixture was cooled to 5° C. and added with 2 ml of a tetrahydrofuran solution of 287 mg (1.0 mmol) of (3R,4R)-4-acetoxy-3-[(R)-1-tert-butyldimethylsilyloxyethyl]azetidin-2-one at the same temperature. After stirring for 10 minutes, 10 ml of ethyl acetate was added to the reaction mixture, followed by the dropwise addition of 2ml of a 10% aqueous solution of citric acid. After separation, the organic layer was washed with 2 ml of a saturated aqueous solution of sodium bicarbonate and 2 ml of a saturated aqueous solution of sodium chloride, dried over anhydrous magnesium sulfate and distilled to remove the solvent. The residue was purified by column chromatography, whereby 83 mg (0.18 mmol) of a condensation product was obtained (yield: 18%, β:α=64:46).

Example 23
Preparation of 3-{(2R)-2-[(3S,4R)-3-[(1R)-1-tert-butyldimethylsilyloxyethyl]-2-oxoazetidin-4-yl]propionyl}-5,5-dimethyl-2,2-pentamethyleneoxazin-4-one

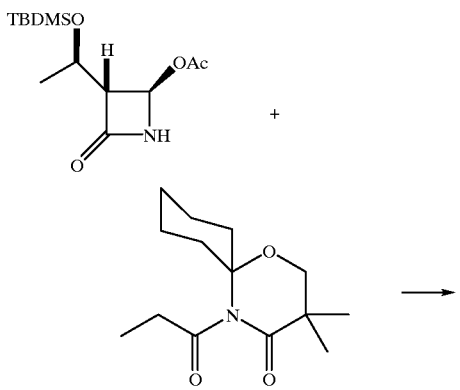

Under a nitrogen atmosphere, 1.85 ml (1.3 mmol) of a 0.70M tetrahydrofuran solution of sec-butylmagnesium chloride was added to a solution of 303 mg (1.0 mmol) of 5,5-dimethyl-3-propionyl-2,2-pentamethyleneoxazin-4-one in 3 ml of tetrahydrofuran at room temperature, followed by stirring at room temperature for 90 minutes. After cooling to 5° C., a solution of 287 mg (1.0 mmol) of (3R,4R)-4-acetoxy-3-[(R)-1-tert-butyldimethylsilyloxyethyl]-azetidin-2-one in 2 ml of tetrahydrofuran was slowly added dropwise, and the reaction mixture was stirred for further 30 minutes. Then, 2 ml of 2N-hydrochloric acid was added, followed by extraction with 10 ml of ethyl acetate. The organic layer was washed with 2 ml of a saturated aqueous solution of sodium bicarbonate, dried over anhydrous magnesium sulfate and distilled to remove the solvent. The residue was purified by column chromatography, whereby 283 mg (0.59 mmol) of a condensation product was obtained (yield: 59%, β:α=75:25).

Example 24
Preparation of 3-{(2R)-2-[(3S,4R)-3-[(1R)-1-t-butyldimethylsilyloxyethyl]-2-oxoazetidin-4-yl]propionyl}-spiro[2,3-dihydro-4H-1,3-benzoxazin-2,1'-cyclohexan]-4-one

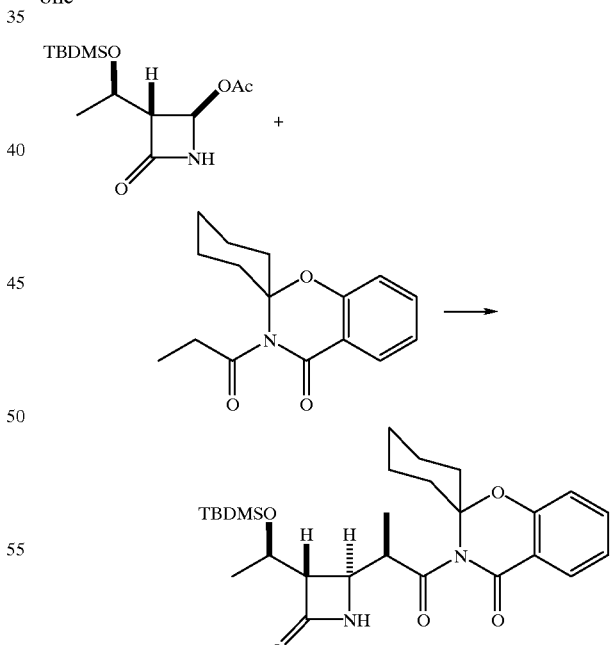

Under a nitrogen atmosphere, 273 mg (1.0 mmol) of 3-propionyl-spiro[2,3-dihydro-4H-1,3-benzoxazine-2,1'-cyclohexan]-4-one was charged in a 30-ml three-necked flask to dissolve it in 2 ml of tetrahydrofuran. To the resulting solution, 2.44 ml (2.2 mmol) of a tetrahydrofuran solution (0.9M) of n-butylmagnesium chloride was slowly added dropwise at room temperature. The resulting mixture was reacted for 25 minutes under the same conditions. After cooling to 5° C., 2 ml of a tetrahydrofuran solution of 287 mg (1.0 mmol) of (3R,4R)-4-acetoxy-3-[(R)-1-tert-butyldimethylsilyloxyethyl]azetidin-2-one was added at the same temperature. The resulting mixture was stirred for 15 minutes, added with 10 ml of ethyl acetate and then added dropwise with 2 ml of a 10% aqueous solution of citric acid. After separation, the organic layer was washed with 2 ml of a saturated aqueous solution of sodium bicarbonate and 2 ml of a saturated aqueous solution of sodium chloride, dried over anhydrous magnesium sulfate and distilled to remove the solvent. The residue was purified by column chromatography, whereby 263 mg (0.53 mmol) of a condensation product was obtained (yield: 53%, β:α=92:8).

Example 25

Preparation of 3-{(2R)-2-[(3S,4R)-3-[(1R)-1-t-butyldimethylsilyloxyethyl]-2-oxoazetidin-4-yl]propionyl}-spiro[2,3-dihydro-4H-1,3-naphthoxazin-2,1'-cyclohexan]-4-one

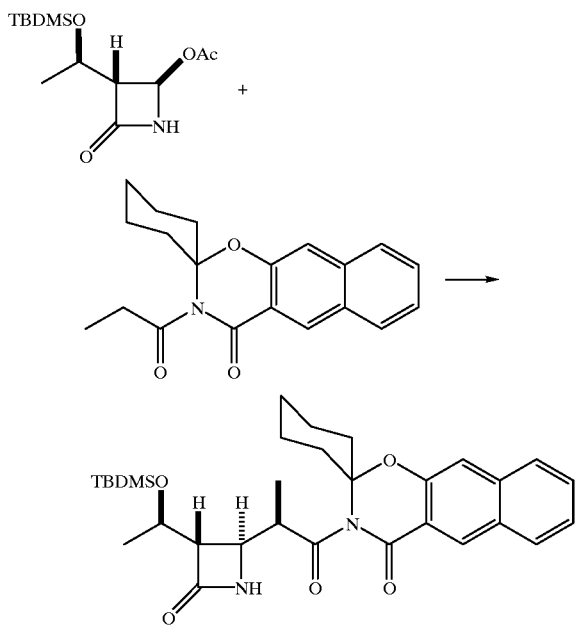

Under a nitrogen atmosphere, 323 mg (1.0 mmol) of 3-propionyl-spiro[2,3-dihydro-4H-1,3-naphthoxazine-2,1'-cyclohexan]-4-one was charged in a 30-ml three-necked flask to dissolve it in 2 ml of tetrahydrofuran. To the resulting solution, 2.2 ml (2.2 mmol) of a tetrahydrofuran solution (1.0M) of phenylmagnesium bromide was slowly added dropwise at room temperature. The resulting mixture was reacted for 20 minutes under the same conditions. After cooling to 5° C., 2 ml of a tetrahydrofuran solution of 287 mg (1.0 mmol) of (3R,4R)-4-acetoxy-3-[(R)-1-tert-butyldimethylsilyloxyethyl]azetidin-2-one was added at the same temperature. The resulting mixture was stirred for 10 minutes, added with 10 ml of ethyl acetate and then added dropwise with 2 ml of a 10% aqueous solution of citric acid. After separation, the organic layer was washed with 2 ml of a saturated aqueous solution of sodium bicarbonate and 2 ml of a saturated aqueous solution of sodium chloride, dried over anhydrous magnesium sulfate and distilled to remove the solvent. The residue was purified by column chromatography, whereby 258 mg of a condensation product was obtained (yield: 47%, β:α=95:5).

Example 26

Preparation of 3-{(2R)-2-[(3S,4R)-3-[(1R)-1-tert-butyldimethylsilyloxyethyl]-2-oxoazetidin-4-yl]propionyl}-3,3,4,4-tetramethylazetidin-2-one

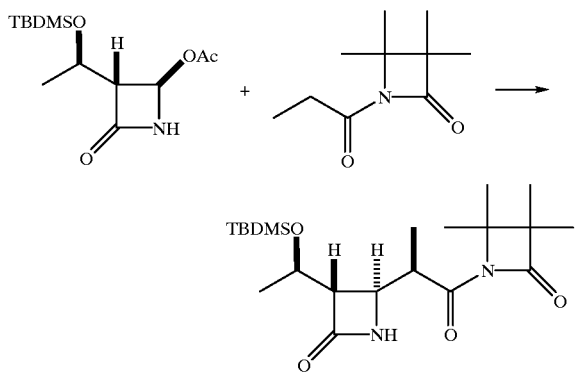

Under a nitrogen atmosphere, 2.75 ml (2.2 mmol) of a 0.80M tetrahydrofuran solution of t-butylmagnesium chloride was added to a solution of 183 mg (1.0 mmol) of N-propionyl-3,3,4,4-tetramethylazetidin-2-one in 1 ml of tetrahydrofuran at room temperature, followed by heating to 50° C. After stirring for 60 minutes, the reaction mixture was cooled to the room temperature. To the reaction mixture, a solution of 287 mg of (3R,4R)-4-acetoxy-3-[(R)-1-tert-butyldimethylsilyloxyethyl]-azetidin-2-one in 1 ml of tetrahydrofuran was slowly added dropwise. The resulting mixture was stirred for further 30 minutes, and 4 ml of 2N-hydrochloric acid was added, followed by extraction with 10 ml of ethyl acetate. The organic layer was washed with 4 ml of a saturated aqueous solution of sodium bicarbonate, dried over anhydrous magnesium sulfate and distilled to remove the solvent. The residue was purified by column chromatography, whereby 295 mg of a condensation product was obtained (yield: 72%, β:α=40:60).

Example 27

Preparation of 3-{(2R)-2-[(3S,4R)-3-[(1R)-1-tert-butyldimethylsilyloxyethyl]-2-oxoazetidin-4-yl]propionyl}-N-cyclohexyl-p-toluenesulfonamide

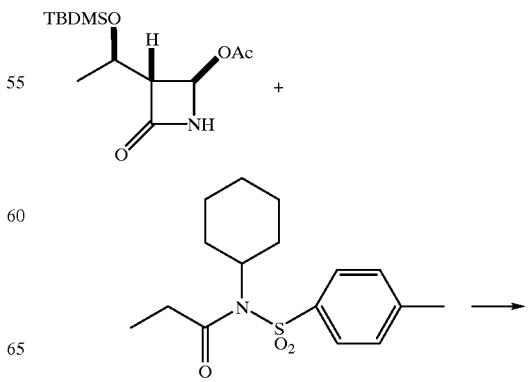

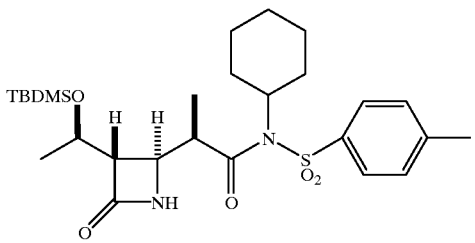

Under a nitrogen atmosphere, 309 mg (1.0 mmol) of N-cyclohexyl-N-p-toluenesulfonylpropionamide was charged in a 30-ml three-necked flask to dissolve it in 2 ml of tetrahydrofuran. To the resulting solution, 2.2 ml (2.2 mmol) of a tetrahydrofuran solution (0.99M) of sec-butylmagnesium chloride was slowly added dropwise at room temperature. The resulting mixture was reacted for 25 minutes under the same conditions. After cooling to 5° C., 2 ml of a tetrahydrofuran solution of 287 mg (1.0 mmol) of (3R,4R)-4-acetoxy-3-[(R)-1-tert-butyldimethylsilyloxyethyl]azetidin-2-one was added at the same temperature. The resulting mixture was stirred for 10 minutes, added with 10 ml of ethyl acetate and then added dropwise with 2 ml of a 10% aqueous solution of citric acid. After separation, the organic layer was washed with 2 ml of a saturated aqueous solution of sodium bicarbonate and 2 ml of a saturated aqueous solution of sodium chloride, dried over anhydrous magnesium sulfate and distilled to remove the solvent. The residue was purified by column chromatography, whereby 339 mg of a condensation product was obtained (yield: 63%, β:α=92:8).

Examples 28 to 38

In each of Examples 28 to 38, the substrate shown in Table 2 was reacted in a similar manner to Example 27, whereby the corresponding β-methyl form was obtained at high selectivity (in Table 2, Pr, Bu, Bn and Ph mean propyl, butyl, benzyl and phenyl groups, respectively).

TABLE 2

| Example | R' | R" | β-methyl form:α-methyl form | Yield (%) |
|---|---|---|---|---|
| 28 | cyclopentyl | 4-CH$_3$—C$_6$H$_4$— | 85:15 | 35 |
| 29 | iso-Pr | 4-CH$_3$—C$_6$H$_4$— | 84.5:15.5 | 30 |
| 30 | tert-Bu | 4-CH$_3$—C$_6$H$_4$— | 90:10 | 36 |
| 31 | Ph | 4-CH$_3$—C$_6$H$_4$— | 88:12 | 49 |
| 32 | Bn | 4-CH$_3$—C$_6$H$_4$— | 63:37 | 30 |
| 33 | (S)-phenethyl | 4-CH$_3$—C$_6$H$_4$— | 61:39 | 55 |
| 34 | (R)-phenethyl | 4-CH$_3$—C$_6$H$_4$— | 97:3 | 78 |
| 35 | cyclohexyl | 4-MeO—C$_6$H$_4$— | 84:16 | 57 |
| 36 | cyclohexyl | 4-tert-Bu—C$_6$H$_4$— | 88:12 | 54 |
| 37 | cyclohexyl | 2-Naphthyl | 86:14 | 56 |
| 38 | cyclohexyl | 4-Br—C$_6$H$_4$— | 83:17 | 48 |

Reference, Example 1

Preparation of (R)-2-[(3S,4S)-3-[(R)-1-tert-butyldimethylsilyloxyethyl]-2-oxoazetidin-4-yl]propionic acid To a tetrahydrofuran solution (2:1, 3.5 ml) of 3-{(2R)-2-[(3S,4R)-3-[(1R)-1-tert-butyldimethylsilyloxyethyl]-2-oxoazetidin-4-yl]propionyl}-N-cyclohexyl-p-toluenesulfonamide (218 mg, 0.4 mmol, β:α=88:12), 0.5N aqueous sodium hydroxide (1.8 ml) was added dropwise at room temperature, followed by stirring for 3 hours at the same temperature. To the reaction mixture, 5 ml of water was then poured and the resulting mixture was washed with methylene chloride. The aqueous layer was acidified to pH 2 with 2N-hydrochloric acid. The crystals so precipitated were collected by filtration, washed with water, and then dried under reduced pressure, whereby 84 mg (β:α=89:11) of the colorless title compound was obtained (yield: 69%).

Reference Example 2

Preparation of (R)-2-[(3S,4S)-3-[(R)-1-tert-butyldimethylsilyloxyethyl]-2-oxoazetidin-4-yl]propionic acid To a solution of 3-{(2R)-2-[(3S,4R)-3-[(1R)-1-t-butyldimethylsilyloxyethyl]-2-oxoazetidin-4-yl]propionyl}-(3aS-cis)-3,3a,8,8a-tetrahydro-2H-indeno[1,2-d]oxazol-2-one (308 mg) dissolved in a methanol-water solvent mixture (2:1, 3 ml), 30% hydrogen peroxide water (0.15 g, 1.35 mmol) was added at room temperature. To the resulting mixture, a 28% aqueous solution of sodium hydroxide (0.12 g, 0.81 mmol) was added dropwise at the same temperature. Stirring was continued until the full consumption of the starting material was confirmed by HPLC. After the completion of the reaction, cool water (10 ml) was added to the reaction mixture. After washing with methylene chloride (5 ml), the pH of the mixture was adjusted to 2 with 35% hydrochloric acid. The crystals so precipitated were collected by filtration, washed with water and then dried, whereby 160 mg (β:α=96:4) of the colorless title compound was obtained (yield: 89%).

Different from the conventional process which requires a reagent complex of a base and a Lewis acid or predetermined low-temperature reaction conditions, the preparation process according to the present invention does not require them but employs only an easily-handled and inexpensive magnesium compound which is represented by the formula (III) so that it is an excellent process from the industrial point of view.

In addition, when R$^2$ of the amide compound is represented by the formula (II) is an alkyl group such as methyl, a β-form which is important as an intermediate for the synthesis of a carbapenem compound can be prepared selectively by adjusting the molar ratio or selecting an auxiliary group as needed.

While the invention has been described in detail and with reference to specific embodiments thereof, it will be apparent to one skilled in the art that various changes and modifications can be made therein without departing from the spirit and scope thereof.

What is claimed is:

1. A process for the preparation of a 4-substituted azetidinone derivative represented by the following formula (IV):

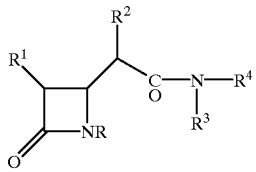

(IV)

wherein R represents a hydrogen atom or a protecting group for N, $R^1$ represents a lower alkyl group which may be substituted by a protected or unprotected hydroxyl group, $R^2$ represents a hydrogen atom or a lower $C_{1-4}$ alkyl group, $R^3$ represents (1) a $C_{1-12}$ alkyl group, (2) a $C_{2-5}$ alkenyl group, (3) a $C_{1-6}$ organosilyl group selected from the group consisting of tert-butyldimethylsilyl, tert-butyldiphenylsilyl, triethylsilyl, triisopropylsilyl, dimethylthexylsilyl dimethylhexylsilyl and trimethylsilyl, (4) a phenyl group which may be substituted by a lower $C_{1-4}$ alkyl group, a lower $C_{1-4}$ alkoxy group, a nitro group or a halogen atom, (5) a $C_{6-13}$ aralkyl group which may be substituted by a lower $C_{1-4}$ alkyl group, (6) a 5- to 8-membered alicyclic group which may be substituted by a lower $C_{1-4}$ alkyl group or (7) a naphthyl group, and $R^4$ is an electron withdrawing group selected from a group consisting of $-SO_2R^8$, $-C(=X)-Y-R^9$, $-C(=X)-R^{10}$, with the proviso that when $R^4$ is

$R^8$ represents (1) a $C_{1-12}$ alkyl group, (2) a phenyl group which may be substituted by a lower $C_{1-4}$ alkyl group, a lower $C_{1-4}$ alkoxy group, a nitro group or a halogen atom, (3) a benzyl group which may be substituted by a lower $C_{1-4}$ alkyl group, (4) a 5- to 7-membered alicyclic group which may be substituted by a lower $C_{1-4}$ alkyl group or (5) a naphthyl group; or $R^3$ and $R^4$ may form a heterocyclic ring together with the adjacent nitrogen atom, of the formula:

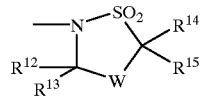

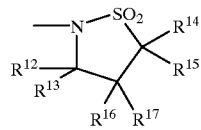

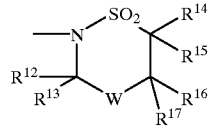

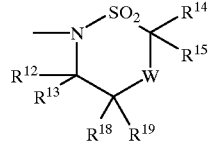 or

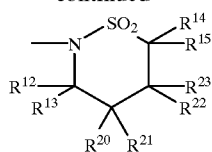

wherein W represents an oxygen atom or a sulfur atom, and $R^{12}$ to $R^{23}$ are the same or different and each independently represents (1) a hydrogen atom, (2) a $C_{1-2}$ alkyl group, (3) a phenyl group which may be substituted by a lower $C_{1-4}$ alkyl group, a lower $C_{1-4}$ alkoxy group, a nitro group or a halogen atom, (4) a benzyl group which may be substituted by a lower $C_{1-4}$ alkyl group, (5) a 5- to 7-membered alicyclic group which may be substituted by a lower $C_{1-4}$ alkyl group, or (6) a naphthyl group; or (7) any two of $R^{12}$ to $R^{23}$ on the same carbon atom may be coupled together to form a $C_{4-6}$ alkylene group, (8) any two of $R^{12}$ and $R^{23}$ on the adjacent carbon atoms may form, together with the carbon atoms, an aromatic ring which may have a substituent wherein said substituent is a lower $C_{1-4}$ alkyl group, a lower $C_{1-4}$ alkoxy group, an aryl group, a hydroxy group or a halogen atom, (9) any two of $R^{12}$ to $R^{23}$ on the adjacent carbon atoms may be coupled together to form a $C_{3-6}$ alkylene group, or (10) any two of $R^{12}$ to $R^{23}$ on the adjacent carbon atoms may form, together with the carbon atoms, a polycyclic group selected form the group consisting of: indan, norbornane, and 1,2,3,4-tetrahydronaphthalene;

when $R^4$ is

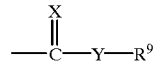

X represents an oxygen atom, a sulfur atom or an $NR^{11}$ group, wherein $R^{11}$ represents a substituted or unsubstituted alkyl group or a substituted or unsubstituted phenyl group, Y represents an oxygen atom or a sulfur atom, $R^9$ represents (1) a $C_{1-12}$ alkyl group, (2) a phenyl group which may be substituted by a lower $C_{1-4}$ alkyl group, a lower $C_{1-4}$ alkoxy group, a nitro group or a halogen atom, (3) a benzyl group which may be substituted by a lower $C_{1-4}$ alkyl group, (4) a 5- to 7-membered alicyclic group which may be substituted by a lower $C_{1-4}$ alkyl group or (5) a naphthyl group; or $R^4$ may form a 4- to 6-membered ring together with $R^3$ and the adjacent nitrogen of the formula:

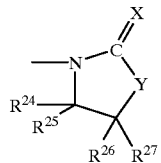

or

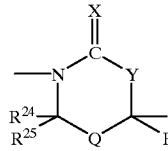

-continued

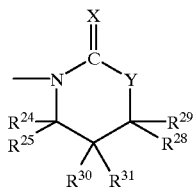

wherein X and Y have the same meanings as defined above, Q represents an oxygen atom or a sulfur atom, and $R^{24}$ to $R^{32}$ are the same or different and each independently represents (1) a hydrogen atom, (2) a $C_{1-12}$ alkyl group, (3) a phenyl group which may be substituted by a lower $C_{1-4}$ alkyl group, a lower $C_{1-4}$ alkoxy group, a nitro group or a halogen atom, (4) a benzyl group which may be substituted by a lower $C_{1-4}$ alkyl group, (5) a 5- to 7-membered alicyclic group which may be substituted by a lower $C_{1-4}$ alkyl group, or (6) a naphthyl group; or (7) any two of $R^{24}$ to $R^{31}$ on the same carbon atom may be coupled together to form a $C_{4-6}$ alkylene group, (8) any two of $R^{24}$ to $R^{31}$ on the adjacent carbon atoms may form, together with the carbon atoms, an aromatic ring which may have a substituent wherein said substituent is a lower $C_{1-4}$ alkyl group, a lower $C_{1-4}$ alkoxy group, an aryl group, a hydroxy group or a halogen atom, (9) any two of $R^{24}$ to $R^{31}$ on the adjacent carbon atoms maybe coupled together to form a $C_{3-6}$ alkylene, group, or (10) any two of $R^{24}$ to $R^{31}$ on the adjacent carbon atoms may form, together with the carbon atoms, a polycyclic group selected from the group consisting of: indan, norbornane, and 1,2,3,4-tetrahydronaphthalene;

when $R^4$ is

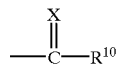

X represents an oxygen atom, a sulfur atom or an $NR^{11}$ group, wherein $R^{11}$ represents a substituted or unsubstituted alkyl group or a substituted or unsubstituted phenyl group, Y represents an oxygen atom or a sulfur atom, $R^{10}$ represents (1) a $C_{1-12}$ alkyl group, (2) a phenyl group which may be substituted by a lower $C_{1-4}$ alkyl group, a lower $C_{1-4}$ alkoxy group, a nitro group or a halogen atom, (3) a benzyl group which may be substituted by a lower $C_{1-4}$ alkyl group, (4) a 5- to 7-membered alicyclic group which may be substituted by a lower $C_{1-4}$ alkyl group or (5) a naphthyl group; or $R^4$ may form a 4- to 6-membered ring together with $R^3$ and the adjacent nitrogen of the formula:

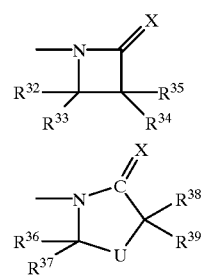

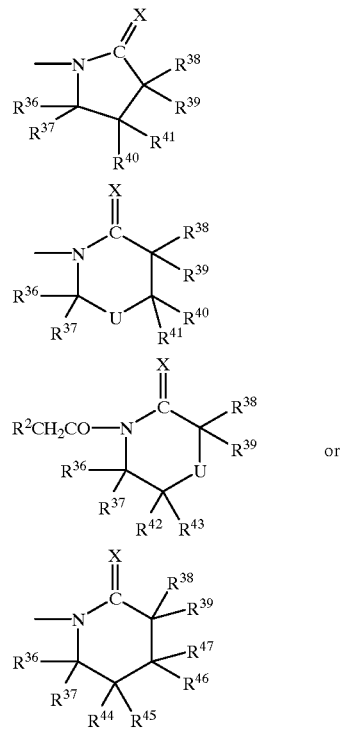

wherein X has the same meaning as defined above, U represents an oxygen atom or a sulfur atom, and $R^{32}$ to $R^{47}$ are the same or different and each independently represents (1) a hydrogen atom, (2) a $C_{1-12}$ alkyl group, (3) a phenyl group which may be substituted by a lower $C_{1-4}$ alkyl group, a lower $C_{1-4}$ alkoxy group, a nitro group or a halogen atom, (4) a benzyl group which may be substituted by a lower $C_{1-4}$ alkyl group, (5) a 5- to 7-membered alicyclic group which may be substituted by a lower $C_{1-4}$ alkyl group, or (6) a naphthyl group; or (7) any two of $R^{32}$ to $R^{47}$ on the same carbon atom may be coupled together to form a $C_{4-6}$ alkylene group, (8) any two of $R^{32}$ to $R^{47}$ on the adjacent carbon atoms may form, together with the carbon atoms, an aromatic ring which may have a substituent wherein said substituent is a lower $C_{1-4}$ alkyl group, a lower $C_{1-4}$ alkoxy group, an aryl group, a hydroxy group or a halogen atom, (9) any two of $R^{32}$ to $R^{47}$ on the adjacent carbon atoms may be coupled together to form a $C_{3-6}$ alkylene group, or (10) any two of $R^{32}$ to $R^{47}$ on the adjacent carbon atoms may form, together with the carbon atoms, a polycyclic group selected from the group consisting of: indan, norbornane, and 1,2,3,4-tetrahydronaphthalene;

which comprises reacting an azetidinone derivative represented by the following formula (I):

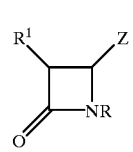

(I)

wherein R represents a hydrogen atom or a protecting group for N, Z represents an eliminative group and $R^1$ has the same meaning as defined above, with an amide compound represented by the following formula (II):

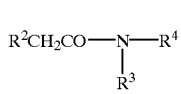  (II)

wherein $R^2$, $R^3$ and $R^4$ have the same meaning as defined above, in the presence of a magnesium compound represented by the following formula (III):

  (III)

wherein $R^5$ represents (1) a $C_{1-12}$ alkyl group, (2) a $C_{2-5}$ alkenyl group, (3) a 5- to 8-member alicyclic group which may be substituted by a lower $C_{1-4}$ alkyl group, (4) a phenyl group which may be substituted by a lower $C_{1-4}$ alkyl group, a lower $C_{1-4}$ alkoxy group or a halogen atom, or (5) a benzyl group which may be substituted by a lower $C_{1-4}$ alkyl group, a lower $C_{1-4}$ alkoxy group or a halogen atom, and $R^6$ represents (1) a halogen atom, (2) a methanesulfonyloxy group, (3) a benzenesulfonyloxy group, (4) a p-toluenesulfonyloxy group, (5) a trifluoromethanesulfonyloxy group, (6) an acetoxy group which may be substituted by a halogen atom or a cyano group, or (7) an $OR^7$ group wherein $R^7$ represents a lower $C_{1-4}$ alkyl group, a substituted or unsubstituted phenyl group or a substituted or unsubstituted benzyl group.

2. A process according to claim 1, wherein the magnesium compound represented by the formula (III) is a compound selected from the group consisting of methylmagnesium chloride, methylmagnesium bromide, methylmagnesium iodide, methylmagnesium methanesulfonate, methylmagnesium tert-butoxide, ethylmagnesium chloride, ethylmagnesium bromide, ethylmagnesium iodide, ethylmagnesium methanesulfonate, ethylmagnesium tert-butoxide, propylmagnesium chloride, propylmagnesium bromide, propylmagnesium iodide, propylmagnesium methanesulfonate, propylmagnesium tert-butoxide, iso-propylmagnesium chloride, iso-propylmagnesium bromide, iso-propylmagnesium iodide, iso-propylmagnesium methanesulfonate, iso-propylmagnesium tert-butoxide, n-butylmagnesium chloride, n-butylmagnesium bromide, n-butylmagnesium iodide, n-butylmagnesium methanesulfonate, n-butylmagnesium tert-butoxide, sec-butylmagnesium chloride, sec-butylmagnesium bromide, sec-butylmagnesium iodide, sec-butylmagnesium methanesulfonate, sec-butylmagnesium tert-butoxide, iso-butylmagnesium chloride, iso-butylmagnesium bromide, iso-butylmagnesium iodide, iso-butylmagnesium methanesulfonate, iso-butylmagnesium tert-butoxide, tert-butylmagnesium chloride, tert-butylmagnesium bromide, tert-butylmagnesium iodide, tert-butylmagnesium methanesulfonate, tert-butylmagnesium tert-butoxide, phenylmagnesium chloride, phenylmagnesium bromide, phenylmagnesium iodide, phenylmagnesium methanesulfonate, phenylmagnesium tert-butoxide, p-tolylmagnesium chloride, p-tolylmagnesium bromide, p-tolylmagnesium iodide, p-tolylmagnesium methanesulfonate, p-tolylmagnesium tert-butoxide, benzylmagnesium chloride, benzylmagnesium bromide, benzylmagnesium iodide, benzylmagnesium methanesulfonate and benzylmagnesium tert-butoxide.

3. A process according to claim 1, wherein the amide compound represented by the formula (V) is a compound selected from the amide compounds represented by the following formulas (VIII), (IX), (X), (XI) and (XII):

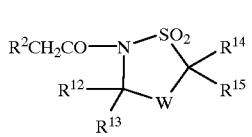  (VIII)

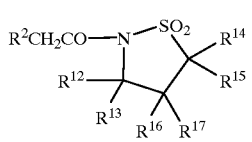  (IX)

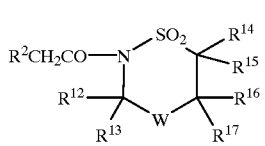  (X)

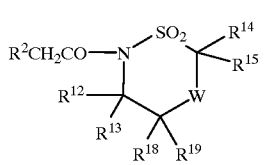  (XI)

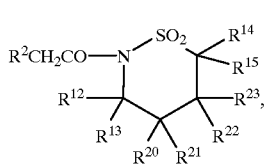  (XII)

wherein $R^2$, W and $R^{12}$ to $R^{23}$ are as defined in claim 1.

4. A process according to claim 1, wherein the amide compound represented by the formula (VI) is a compound selected from the amide compounds represented by the following formulas (XIII), (XIV) and (XV):

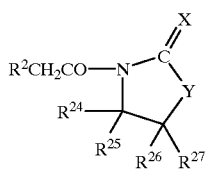  (XIII)

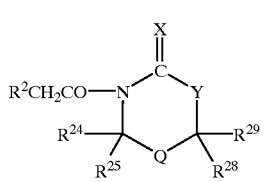  (XIV)

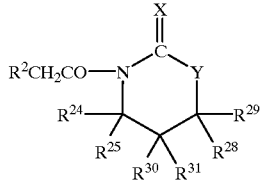  (XV)

wherein $R^2$, X, Y, Q and $R^{24}$ to $R^{31}$ are as defined in claim 1.

5. A process according to claim 1, wherein the amide compound represented by the formula (VII) is a compound selected from the amide compounds represented by the following formulas (XVI), (XVII), (XVIII), (XIX), (XX) and (XXI):

(XVI)

$R^2CH_2CO-N$ ... $R^{32}, R^{33}, R^{34}, R^{35}$, X (XVII)

$R^2CH_2CO-N$ ... $R^{36}, R^{37}, R^{38}, R^{39}$, U, X (XVIII)

$R^2CH_2CO-N$ ... $R^{36}, R^{37}, R^{38}, R^{39}, R^{40}, R^{41}$, X (XIX)

$R^2CH_2CO-N$ ... $R^{36}, R^{37}, R^{38}, R^{39}, R^{40}, R^{41}$, U, X (XX)

$R^2CH_2CO-N$ ... $R^{36}, R^{37}, R^{38}, R^{39}, R^{42}, R^{43}$, U, X (XXI)

$R^2CH_2CO-N$ ... $R^{36}, R^{37}, R^{38}, R^{39}, R^{44}, R^{45}, R^{46}, R^{47}$, X wherein $R^2$, X, U and $R^{32}$ to $R^{47}$ are as defined in claim 1.

6. The process of claim 1 wherein $R^7$ is a substituted benzyl group and the substitutent is selected from the group consisting of: a lower $C_{1-4}$ alkyl group, a lower $C_{1-4}$ alkoxy group, and a halogen atom.

7. A process according to claim 4, wherein the amide compound is represented by the formula (XIII).

8. A process according to claim 5, wherein the amide compound is a compound selected from the group consisting of the amide compounds represented by the formulas (XVI), (XVII) and (XIX).

9. A process according to claim 1, wherein the 4-substituted azetidinone derivative represented by Formula (IV), is selected from the group consisting of:

3-{(2R)-2-[(3S,4R)-3-[(1R)-1-tert-butyldimethylsilyloxyethyl]-2-oxoazetidin-4-yl]propionyl}-5,5-dimethyl-2,2-pentamethyleneoxazolin-4-one, 3-{(2R)-2-[(3S,4R)-3-[(1R)-1-tert-butyldimethylsilyloxyethyl]-2-oxoazetidin-4-yl]propionyl}-2,2-dibenzyl-5,5-dimethyloxazolin-4-one, 3-{(2R)-2-[(3S,4R)-3-[(1R)-1-tert-butyldimethylsilyloxyethyl]-2-oxoazetidin-4-yl]propionyl}1-4,4-dimethyloxazolin-4-one, 3-{(2R)-2-[(3S,4R)-3-[(1R)-1-tert-butyldimethylsilyloxyethyl]-2-oxoazetidin-4-yl]propionyl}-4(S)-4-phenyloxazolin-4-one, 3-{(2R)-2-[(3S,4R)-3-[(1R)-1-tert-butyldimethylsilyloxyethyl]-2-oxoazetidin-4-yl]propionyl}-4(S)-4-benzyloxazolin-4-one, 3-{(2R)-2-[(3S,4R)-3-[(1R)-1-tert-butyldimethylsilyloxyethyl]-2-oxoazetidin-4-yl]propionyl}-4(S)-4-isopropyloxazolin-4-one, 3-{(2R)-2-[(3S,4R)-3-[(1R)-1-t-butyldimethylsilyloxyethyl]-2-oxoazetidin-4-yl]propionyl}-(3aS-cis)-3,3a,8,8a-tetrahydro-2H-indeno[1,2-d]oxazol-2-one, 3-{(2R)-2-[(3S,4R)-3-[(1R)-1-t-butyldimethylsilyloxyethyl]-2-oxoazetidin-4-yl]propionyl}-(3aR-cis)-3,3a,8,8a-tetrahydro-2H-indeno[1,2-d]oxazol-2-one, 3-{(2R)-2-[(3S,4R)-3-[(1R)-1-tert-butyldimethylsilyloxyethyl]-2-oxoazetidin-4-yl]propionyl}-5,5-dimethyl-2,2-pentamethyleneoxazin-4-one, 3-{(2R)-2-[(3S,4R)-3-[(1R)-4-t-butyldimethylsilyloxyethyl]-2-oxoazetidin-4-yl]propionyl}-spiro[2,3-dihydro-4H-1,3-benzoxazin-2,1'-cyclohexan]-4-one, 3-{(2R)-2-[(3S,4R)-3-[(1R)-1-t-butyldimethylsilyloxyethyl]-2-oxoazetidin-4-yl]propionyl}-spiro[2,3-dihydro-4H-1,3-naphthoxazin-2,1'-cyclohexan]-4-one, 3-{(2R)-2-[(3S,4R)-3-[(1R)-1-tert-butyldimethylsilyloxyethyl]-2-oxoazetidin-4-yl]propionyl}3,3,4,4-tetramethylazetidin-2-one; and 3-{(2R)-2-[(3S,4R)-3-[(1R)-1-tert-butyldimethylsilyloxyethyl]-2-oxoazetidin-4-yl]propionyl}-N-cyclohexyl-p-toluenesulfonamide, 3-{(2R)-2-[(3S,4R)-3-[(1R)-1-tert-butyldimethylsilyloxyethyl]-2-oxoazetidin-4-yl]propionyl}-N-cyclopentyl-p-toluenesulfonamide, 3-{(2R)-2-[(3S,4R)-3-[(1R)-1tert-butyldimethylsilyloxyethyl]-2-oxoazetidin-4-yl]propionyl}-N-isopropyl-p-toluenesulfonamide, 3-{(2R)-2-[(3S,4R)-3-[(1R)-1-tert-butyldimethylsilyloxyethyl]-2-oxoazetidin-4-yl]propionyl}-N-tert-butyl-p-toluenesulfonamide, 3-{(2R)-2-[(3S,4R)-3-[(1R)-1-tert-butyldimethylsilyloxyethyl]-2-oxoazetidin-4-yl]propionyl}-N-phenyl-p-toluenesulfonamide, 3-{(2R)-2-[(3S,4R)-3-[(1R)-1-tert-butyldimethylsilyloxyethyl]-2-oxoazetidin-4-yl]propionyl}-N-benzyl-p-toluenesulfonamide, 3-{(2R)-2-[(3S,4R)-3-[(1R)-1-tert-butyldimethylsilyloxyethyl]-2-oxoazetidin-4-yl]propionyl}-N-(S)-phenethyl-p-toluenesulfonamide, 3-{(2R)-2-[(3S,4R)-3-[(1R)-1-tert-butyldimethylsilyloxyethyl]-2-oxoazetidin-4-yl]propionyl}-N-(R)-phenethyl-p-toluenesulfonamide, 3-{(2R)-2-[(3S,4R)-3-[(1R)-1-tert-butyldimethylsilyloxyethyl]-2-oxoazetidin-4-yl]propionyl}-N-cyclohexyl-4-methoxybenzenesulfonamide, 3-{(2R)-2-[(3S,4R)-3-[(1R)-1-tert-butyldimethylsilyloxyethyl]-2-oxoazetidin-4-yl]propionyl}-N-cyclohexyl-4-tert-buthylbenzenesulfonamide, 3-{(2R)-2-[(3S,4R)-3-[(1R)-1-tert-butyldimethylsilyloxyethyl]-2-oxoazetidin-4-yl]propionyl}-N-cyclohexyl-2-Naphthalenesulfonamide, and 3-{(2R)-2-[(3S,4R)-3-[(1R)-1-tert-butyldimethylsilyloxyethyl]-2-oxoazetidin-4-yl]propionyl}-N-cyclohexyl-4-bromebenzenesulfonamide.

10. A process according to claim 6, wherein $R^7$ is a substituted benzyl group and the substituent is a lower $C_{1-4}$ alkyl group selected from the group consisting of: methyl, ethyl, propyl, isopropyl, butyl, isobutyl, sec-butyl, and tert-butyl.

11. A process according to claim 1, wherein the amide is selected from the group consisting of:

N-cyclohexyl-N-p-toluenesulfonylpropionamide,
N-cyclopentyl-N-p-toluenesulfonylpropionamide,
N-isopropyl-N-p-toluenesulfonylpropionamide,
N-(tert-butyl)-N-p-toluenesulfonylpropionamide,
N-phenyl-N-p-toluenesulfonylpropionamide,
N-benzyl-N-p-toluenesulfonylpropionamide,
N-[(S)-phenylethyl]-N-p-toluenesulfonylpropionamide,
N-[(R)-phenylethyl]-N-p-toluenesulfonylpropionamide,
N-cyclohexyl-N-4-methoxybenzenesulfonylpropionamide,
N-cyclohexyl-N-4-tert-butylbenzenesulfonylpropionamide,
N-cyclohexyl-N-2-naphthalenesulfonylpropionamide,
N-cyclohexyl-N-4-bromebenzenesulfonylpropionamide,
N-(4-chlorophenyl)-N-p-toluenesulfonylpropionamide,
methyl N-methyl-N-propionylcarbamate,
methyl N-methyl-N-propionylthiocarbamate,
methyl N-tert-butyl-N-propionylcarbamate,
methyl N-tert-butyl-N-propionylthiocarbamate,
methyl N-phenyl-N-propionylcarbamate,
methyl N-phenyl-N-propionylthiocarbamate,
N-methyl-N-propionylbenzamide,
N-ethyl-N-propionylbenzamide,
N-isopropyl-N-propionylbenzamide,
N-phenyl-N-propionylbenzamide,
N-propionyl-2-oxa-1,3-sultam,
N-propionyl-1,2-benzisothiazole-2,3-dihydro-3-methyl-1,1-dioxide,
N-propionyl-bornane-10,2-sultam,
N-propionyl-4,1,2-benzoxathiazine-2,3-dihydro-3-methyl-1,1-dioxide,
N-propionyl-1H-4,2,1-benzoxathiazine-2,2-dioxide,
N-propionyl-2,1-benzothiazine-2,2-dioxide,
4-methyl-3-propionyloxazolidin-2-one,
4,4-dimethyl-3-propionyloxazolidin-2-one,
4-phenyl-3-propionyloxazolidin-2-one,
4-benzyl-3-propionyloxazolidin-2-one,
4-isopropyl-3-propionyloxazolidin-2-one,
3-propionyl-(3aS-cis)-3,3a,8,tetrahydro-2H-indeno[1,2-d]oxazol-2-one,
3-propionyl-(3aR-cis)-3,3a,8,tetrahydro-2H-indeno[1,2-d]oxazol-2-one,
N-propionyltetrahydro-1,5,3-dioxazin-2-one, i.e. -dioxazine-,
N-propionyl-tetrahydro-1,3-oxazin-2-one,
N-propionyl-tetrahydro-1,3-oxazin-2-one-4,4-dimethyl,
N-propionyl-3,3,4,4-tetramethylazetidin-2-one,
N-propionyl-azetidin-2-one,
5,5-dimethyl-3-propionyl-2,2-pentamethyleneoxazolidin-4-one,
2,2-dibenzyl5,5-dimethyl-3-propionyloxazolin-4-one,
2-propionyl-5,5-dimethylpyrrolidin-2-one,
1-propionyl-5,5-diethylpyrrolidin-2-one,
1-propionyl-5,5-diisopropylpyrrolidin-2-one,
5,5-dimethyl-3-propionyl-2,2-pentamethyleneoxazin-4-one,
3-propionyl-spiro[2,3-dihydro-4H-1,3-benzoxazin-2,1'-cyclohexan]-4-one,
3-propionyl-spiro[2,3-dihydro-4H-1,3-naphthoxazin-2,1'-cyclohexan]4-one,
N-propionyl-3,4-dihydro-2H-1,4-benzoxazin-3-one, and
N-propionyl-4H-isoquinolizin-1-one.

12. A process according to claim 1, wherein $R^3$ is a $C_{1-12}$ alkyl group selected from the group consisting of: methyl, ethyl, propyl, isopropyl, butyl, isobutyl, sec-butyl, tert-butyl, pentyl, hexyl, heptyl, octyl, decyl, undecyl, and dodecyl.

13. A process according to claim 1, wherein $R^3$ is a $C_{2-5}$ alkenyl group selected from the group consisting of: vinyl, allyl, 1-propenyl, isopropenyl, 1-butenyl, 2-butenyl, and 2-methallyl.

14. A process according to claim 6, wherein $R^7$ is a substituted benzyl group and the substituent is a lower $C_{1-4}$ alkoxy group selected from the group consisting of: methoxy, ethoxy, propoxy, isopropoxy, butoxy, isobutoxy, sec-butoxy, and tert-butoxy.

15. A process according to claim 1, wherein $R^3$ is a substituted phenyl group, the substitutent being selected from the group consisting of: a lower $C_{1-4}$ alkyl group, a lower $C_{1-4}$ alkoxy group, a nitro group, or a halogen atom.

16. A process according to claim 15, wherein the substituent is a lower $C_{1-4}$ alkyl group selected from the group consisting of: methyl, ethyl, propyl, isopropyl, butyl, isobutyl, sec-butyl, and tert-butyl.

17. A process according to claim 15, wherein the substitutent is a lower $C_{1-4}$ alkoxy group selected from the group consisting of: methoxy, ethoxy, propoxy, isopropoxy, butoxy, isobutoxy, sec-butoxy, and tert-butoxy.

18. A process according to claim 15, wherein the substituent is a halogen selected from the group consisting of: fluorine, chlorine, bromine, and iodine.

19. A process according to claim 1, wherein $R^3$ is a $C_{6-13}$ aralkyl group selected from the group consisting of: benzyl, α-phenylethyl, β-phenylethyl, α-phenylpropyl, β-phenylpropyl, γ-phenylpropyl, and naphthymethyl.

20. A process according to claim 19, wherein the lower $C_{1-4}$ alkyl group substituent of the $C_{6-13}$ aralkyl group is selected from the group consisting of: methyl, ethyl, propyl, isopropyl, butyl, isobutyl, sec-butyl, and tert-butyl.

21. A process according to claim 1, wherein $R^3$ is a 5- to 8-membered alicyclic group selected from the group consisting of: cyclopentyl, cyclohexyl, cycloheptyl, and cyclooctyl.

22. A process according to claim 1, wherein the lower $C_{1-4}$ alkyl group substitutent of the 5- to 8-membered alicyclic group is selected from the group consisting of: methyl, ethyl, propyl, isopropyl, butyl, isobutyl, sec-butyl, and tert-butyl.

23. A process according to claim 1, wherein $R^7$ is a substituted phenyl group, the substitutent being selected from the group consisting of: a lower $C_{1-4}$ alkyl group, a lower $C_{1-4}$ alkoxy group, and a halogen atom.

24. A process according to claim 23, wherein $R^7$ is a substituted phenyl group and the substituent is a lower $C_{1-4}$ alkyl group selected from the group consisting of: methyl, ethyl, propyl, isopropyl, butyl, isobutyl, sec-butyl, and tert-butyl.

25. A process according to claim 23, wherein $R^7$ is a substituted phenyl group and the substituent is a lower $C_{1-4}$ alkoxy group selected from the group consisting of: methoxy, ethoxy, propoxy, isopropoxy, butoxy, isobutoxy, sec-butoxy, and tert-butoxy.

26. A process according to claim 23, wherein $R^7$ is a substituted phenyl group and the substituent is a halogen atom selected from the group consisting of: fluorine, chlorine, bromine, and iodine.

27. A process according to claim 6, wherein $R^7$ is a substituted benzyl group and the substituent is a halogen atom selected from the group consisting of: fluorine, chlorine, bromine or iodine.

\* \* \* \* \*